(12) United States Patent
Zapol et al.

(10) Patent No.: US 9,572,833 B2
(45) Date of Patent: Feb. 21, 2017

(54) TREATMENT OF RED BLOOD CELLS

(71) Applicant: The General Hospital Corporation, Boston, MA (US)

(72) Inventors: Warren M. Zapol, Cambridge, MA (US); Binglan Yu, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/356,221

(22) PCT Filed: Nov. 6, 2012

(86) PCT No.: PCT/US2012/063690
§ 371 (c)(1),
(2) Date: May 5, 2014

(87) PCT Pub. No.: WO2013/070592
PCT Pub. Date: May 16, 2013

(65) Prior Publication Data
US 2014/0286921 A1    Sep. 25, 2014

Related U.S. Application Data

(60) Provisional application No. 61/556,661, filed on Nov. 7, 2011.

(51) Int. Cl.
*A61K 33/00* (2006.01)
*A61K 35/18* (2015.01)
*A61M 1/02* (2006.01)

(52) U.S. Cl.
CPC .............. *A61K 33/00* (2013.01); *A61K 35/18* (2013.01); *A61M 1/0281* (2013.01); *A61M 2202/0275* (2013.01); *A61M 2202/0429* (2013.01)

(58) Field of Classification Search
None
See application file for complete search history.

(56) References Cited

U.S. PATENT DOCUMENTS

| 5,396,882 | A | | 3/1995 | Zapol |
| 5,423,738 | A | * | 6/1995 | Robinson ............ A61M 1/3621 604/28 |
| 5,485,827 | A | | 1/1996 | Zapol et al. |
| 5,531,218 | A | | 7/1996 | Krebs |
| 5,536,241 | A | | 7/1996 | Zapol |
| 5,540,233 | A | | 7/1996 | Larsson et al. |
| 5,558,083 | A | | 9/1996 | Bathe et al. |
| 5,570,683 | A | | 11/1996 | Zapol |
| 5,823,180 | A | | 10/1998 | Zapol |
| 5,839,433 | A | | 11/1998 | Higenbottam |
| 5,873,359 | A | | 2/1999 | Zapol et al. |
| 5,885,621 | A | | 3/1999 | Head et al. |
| 5,900,402 | A | | 5/1999 | Shorr |
| 5,904,938 | A | | 5/1999 | Zapol et al. |
| 6,063,027 | A | | 5/2000 | Alving et al. |
| 6,063,407 | A | | 5/2000 | Zapol et al. |
| 6,089,229 | A | | 7/2000 | Bathe et al. |
| 6,103,690 | A | | 8/2000 | Kilbourn et al. |
| 6,139,506 | A | | 10/2000 | Heinonen |
| 6,323,175 | B1 | | 11/2001 | Hsia |
| 6,601,580 | B1 | | 8/2003 | Bloch et al. |
| 6,656,452 | B1 | | 12/2003 | Zapol et al. |
| 6,811,768 | B2 | | 11/2004 | Zapol et al. |
| 6,894,150 | B1 | | 5/2005 | Tye |
| 6,935,334 | B2 | | 8/2005 | Bloch et al. |
| 7,267,817 | B2 | | 9/2007 | Page et al. |
| 7,485,324 | B2 | * | 2/2009 | Miller .................... A61K 33/00 424/405 |
| 7,516,742 | B2 | | 4/2009 | Stenzler et al. |
| 7,530,353 | B2 | | 5/2009 | Choncholas et al. |
| 2002/0037839 | A1 | * | 3/2002 | Stamler et al. ................... 514/6 |
| 2003/0017537 | A1 | | 1/2003 | Weickert et al. |
| 2003/0162693 | A1 | | 8/2003 | Winslow et al. |
| 2005/0234030 | A1 | | 10/2005 | Bartolini et al. |
| 2005/0255178 | A1 | | 11/2005 | Bloch et al. |
| 2006/0182815 | A1 | | 8/2006 | Gladwin et al. |
| 2006/0207594 | A1 | | 9/2006 | Stenzler et al. |
| 2007/0154569 | A1 | | 7/2007 | Gladwin et al. |

(Continued)

FOREIGN PATENT DOCUMENTS

CN    1229677 A    9/1999
JP    2003-532622    11/2003

(Continued)

OTHER PUBLICATIONS

Hess et al. "Blood components: red blood cell hemolysis during blood bank storage: using national quality management data to answer basic scientific questions", Transfusion 49(12): 2599-2603, 2009.*
European Search Report issued in EP12848112 on Jun. 22, 2015 (5 pages).
Bryan-Lluka LJ et al. Nitric oxide donors inhibit 5-hydroxytryptamine (5-HT) uptake by the human 5-HT transporter (SERT). Br J Pharmacol, Sep. 2004;143(1):63-70. Epub Aug. 9, 2004. PMID: 15302679, abstract [retrieved on Jan. 22, 2003], Retrieved from the Internet: <http://wwww.ncbi.nlm.nih.gov/pubmed/15302679.
International Search Report and Written Opinion mailed Feb. 21, 2013 in international application No. PCT/US202/063690, 7 pgs.
International Preliminary Report on Patentability in International Application No. PCT/US2012/063690, 6 pages.

(Continued)

*Primary Examiner* — Emily Cordas
(74) *Attorney, Agent, or Firm* — Fish & Richardson P.C.

(57)  ABSTRACT

Compositions and methods for treating red blood cells are disclosed. The methods include contacting a red blood cell sample ex vivo with an amount of nitric oxide or a nitric oxide-releasing compound sufficient to convert at least a portion of the extracellular ferrous hemoglobin present in the red blood cell sample to ferric hemoglobin. Red blood cells administered to a mammal following the ex vivo treatment have reduced adverse effects on the mammal to which they are administered.

29 Claims, 17 Drawing Sheets

(56) References Cited

U.S. PATENT DOCUMENTS

2010/0239692 A1* 9/2010 Kim-Shapiro ......... A61K 31/58
424/718

FOREIGN PATENT DOCUMENTS

| JP | 2007-505142 | 3/2007 |
|---|---|---|
| WO | WO 93/16721 | 9/1993 |
| WO | WO 98/08500 | 3/1998 |
| WO | 99/01146 | 1/1999 |
| WO | WO 2007/076318 | 12/2000 |
| WO | 01/09616 | 2/2001 |
| WO | 03/066109 | 8/2003 |
| WO | 03/102575 | 12/2003 |
| WO | WO2005/025511 | 3/2005 |
| WO | WO 2006/037491 | 4/2006 |
| WO | WO 2008/063868 | 5/2008 |
| WO | WO2010/144629 | 12/2010 |

OTHER PUBLICATIONS

Gladwin et al., "The biochemistry of nitric oxide, nitrite, and hemoglobin: role in blood flow regulation," Free Radical Biol Med., 2004, 36(6):707-717.

Hataishi et al., "Inhaled nitric oxide decreases infarction size and improves left ventricular function in a murine model of myocardial ischemia-reperfusion injury," Am J Physiol Heart Circ Physiol., 2006, 291(1):H379-84.

Imai, "Mechanisms of vasolidation of so-called nitrite compounds," J. Clin Experimental Med., 1989, 148(2):71-74 (with excerpted English translation).

Kim-Shapiro et al., "Storage lesion: role of red blood cell breakdown," Transfusion, 2011, 51:844-51.

Minneci et al., "Hemolysis-associated endothelial dysfunction mediated by accelerated NO inactivation by decompartmentalized oxyhemoglobin," J Clin Invest., 2005, 115(12):3409-3417.

Muir and Wellman, "Hemoglobin Solutions and Tissue Oxygenation," J Vet Intern Med., 2003, 7:127-135.

Roberts et al., "Inhaled nitric oxide reverses pulmonary vasoconstriction in the hypoxic and acidotic newborn lamb," Circulation Res., 1993, 72:246-254.

Sampei et al., "Role of nitric oxide scavenging in vascular response to cell-free hemoglobin transfusion," Am J Physiol Heart Circ Physiol., May 13, 2005, 289:H1191-H1201.

Sefton et al., "Inhaled nitric oxide attenuates increased pulmonary artery pressure following diaspirin crosslinked hemoglobin (DCLHB) administration," Artificial Cells, Blood Substitutes, and Immobilization Biotechnol., 1999, 27(3):203-213.

Sowemino-Coker, "Red blood cell hemolysis during processing," Transfus Med. Rev., 2002, 16(1):46-60.

Triulzi and Yazer, "Clinical studies of the effect of blood storage on patient outcomes," Transfus Apher Sci., 2010, 43:95-106.

Tsai et al., "Dissociation of local nitric oxide concentration and vasoconstriction in the presence of cell-free hemoglobin oxygen carriers," Blood, Jul. 20, 2006, 108(10):3603-3610.

Donadee et al., "Nitric Oxide Scavenging by Red Blood Cell Microparticles and Cell-Free Hemoglobin as a Mechanism for the Red Cell Storage Lesion," Circulation, Jul. 2011, 124: 465-476.

Japanese Office Action in Japanese Application No. 2014-541155, dated Aug. 22, 2016, 13 pages. (with English translation).

Yu et al., "Endothelial dysfunction enhances vasoconstriction due to scavenging of nitric oxide by a hemoglobin-based oxygen carrier," Anesthesiology, Mar. 2010, 112: 586-594.

* cited by examiner

TREATMENT OF RED BLOOD CELLS

CROSS REFERENCE TO RELATED APPLICATIONS

This application is a U.S. National Phase Application under 35 U.S.C. 371 of International Patent Application No. PCT/US2012/063690, filed on Nov. 6, 2012, which claims priority from provisional application No. 61/556,661, filed Nov. 7, 2011. The content of the foregoing applications are incorporated herein by reference in their entireties.

TECHNICAL FIELD

This invention relates to compositions and methods for treatment of red blood cells prior to administration to a mammal.

BACKGROUND

Transfusion of red blood cells stored for longer than two weeks has been associated with increased rates of infection, a prolonged hospital length of stay, and increased mortality rates in intensive care unit patients and patients undergoing cardiovascular surgery (Triulzi et al., Transfus Apher Sci 2010; 43:95-106). Prolonged storage of red blood cells causes marked biochemical, mechanical, and functional alterations in erythrocytes, termed collectively the "storage lesion" (Kim-Shapiro et al., Transfusion 2011; 51:844-51). Compositions and methods are needed to reduce or eliminate adverse effects associated with transfusion of stored red blood cells.

SUMMARY

The invention is based, at least in part, on the discovery that ex vivo treatment of stored red blood cells with nitric oxide causes extracellular ferrous hemoglobin to be oxidized to ferric hemoglobin, and that this treatment prevents the stored red blood cells from inducing vasoconstriction following their administration to a mammal. Pretreatment of stored red blood cells with nitric oxide or a nitric oxide-releasing compound can be used as a means to reduce or eliminate the occurrence of adverse effects associated with transfusion of stored blood. By treating blood prior to administration to a mammal, the need to treat the mammal post-transfusion to address adverse effects resulting from the transfusion of stored blood may be avoided.

Disclosed are methods of treating a red blood cell sample by contacting a red blood cell sample ex vivo with an amount of nitric oxide or a nitric oxide-releasing compound sufficient to convert at least a portion of the extracellular ferrous hemoglobin present in the red blood cell sample to ferric hemoglobin. Extracellular ferrous hemoglobin encompasses both cell-free hemoglobin and extracellutar hemoglobin-containing microparticles (see Donadee et al., Circulation 2011; 124: 465-76).

Also disclosed are methods of preventing or reducing vasoconstriction in a mammal following administration of red blood cells by administering to a mammal a red blood cell sample that has been contacted ex vivo with an amount of nitric oxide or a nitric oxide-releasing compound sufficient to convert at least a portion of the extracellular ferrous hemoglobin present in the red blood cell sample to ferric hemoglobin.

In some embodiments of the methods described herein, the method does not significantly oxidize the red blood cells in the sample or diminish their oxygen carrying capacity (e.g., less than 20%, less than 15%, less than 10%, or less than 5% of hemoglobin in the red blood cells is converted to methemoglobin).

In some embodiments of the methods described herein, the red blood cell sample has been subjected to one or more of a pump (e.g., negative pressure pump suction), a membrane, and/or air bubbles ex vivo prior to being contacted with nitric oxide or the nitric oxide-releasing compound. In some embodiments of the methods described herein, the red blood cell sample has been subjected to hemodialysis, intraoperative blood salvage, or cardiotomy suction ex vivo prior to being contacted with nitric oxide or the nitric oxide-releasing compound. In these methods, the red blood cells need only be outside of the body of a mammal for a short time (e.g., seconds or minutes) before being subjected to insults that would be render them in need of a treatment with the methods described herein.

A red blood cell sample comprises red blood cells and supernatant or plasma. The red blood cell sample can be, for example, whole blood or packed red blood cells.

The red blood cell sample can be stored ex vivo, for example, for at least 24 hours after removal from a donor and prior to being contacted with nitric oxide or the nitric oxide-releasing compound. In some embodiments, the red blood cell sample is stored ex vivo for at least 7 days, at least 14 days, at least 28 days, at least 42 days, or longer after removal from a donor and prior to being contacted with nitric oxide or the nitric oxide-releasing compound. The red blood cell sample can optionally be diluted in a storage solution prior to storage.

Red blood cells can be derived from an autologous or allogeneic donor prior to administration to a mammal. The red blood cell sample can therefore comprise autologous red blood cells or allogeneic red blood cells. The red blood cell sample can be stored in a variety of storage media (e.g., Adsol). The red blood cell sample can optionally be frozen and thawed prior to treatment with nitric oxide or a nitric oxide-releasing compound.

In some embodiments of the methods described herein, the treatment causes at least 20% (or at least 50% or at least 80%) of extracellular ferrous hemoglobin present in the red blood cell sample to be converted to ferric hemoglobin.

In some embodiments of the methods described herein, the red blood cell sample is contacted with a therapeutic gas comprising gaseous nitric oxide diluted in an inert gas. The concentration of gaseous nitric oxide in the therapeutic gas can be, for example, at least 20 ppm, at least 40 ppm, at least 50 ppm, at least 80 ppm, at least 100 ppm, at least 200 ppm, at least 300 ppm, or at least 500 ppm. In some embodiments, the concentration of gaseous nitric oxide in the therapeutic gas is in the range of 50 ppm to 800 ppm (e.g., 40 ppm to 200 ppm, 80 ppm to 200 ppm, 80 ppm to 500 ppm, 100 ppm to 800 ppm, or 40 ppm to 3,000 ppm). The red blood cell sample can be contacted with the therapeutic gas over the course of a variety of time periods (e.g., at least 1 second, fewer than 5 seconds, fewer than 30 seconds, at least one second but fewer than 5 seconds, at least one second but fewer than 30 seconds, at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 1 hour, at least 2 hours, or longer).

In some embodiments of the methods described herein, the red blood cell sample is contacted with a nitric oxide-releasing compound. The nitric oxide-releasing compound can optionally comprise nitrite. The nitric oxide-releasing compound can be an ultra-short-acting nitric oxide-releasing compound (e.g., 1-[2-(carboxylato)pyrrolidin-1-yl]diazen-1-ium-1,2-diolate or (Z)-1-[N-Methyl-N-[6-(N-methylammoniohexyl)amino]]diazen-1-ium-1,2-diolate) or an intermediate releasing nonoate.

In some embodiments of the methods described herein, the method is performed under sterile conditions. The red blood cell sample can be maintained under sterile conditions from the time it is obtained from a donor and throughout the process of treatment with nitric oxide or a nitric oxide-releasing compound.

In some embodiments of the methods described herein, the red blood cell sample is contacted with nitric oxide as part of an in-line infusion system wherein the red blood cell sample flows from a vessel comprising the sample, contacts a gas-permeable material (e.g., a microporous membrane) in a laminar flow device or a secondary flow gas exchanging device that is connected to a source of nitric oxide in an inert gas and exposes the red blood cell sample to nitric oxide, and is delivered to the mammal after exposure to nitric oxide. The source of nitric oxide can be, for example, a tank comprising compressed nitric oxide gas or an electric nitric oxide generator (with or without an $NO_2$ scavenger).

A mammal treated according to the methods described herein can be a human, a non-human primate, or another mammal such as a dog, cat, horse, cow, pig, sheep, goat, rat, mouse, guinea pig, rabbit, or hamster.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control. Suitable methods and materials are described below, although methods and materials similar or equivalent to those described herein can also be used in the practice or testing of the present invention. The materials, methods, and examples are illustrative only and not intended to be limiting.

Other features and advantages of the invention will be apparent from the following detailed description, and from the claims.

DETAILED DESCRIPTION

Figure 1:
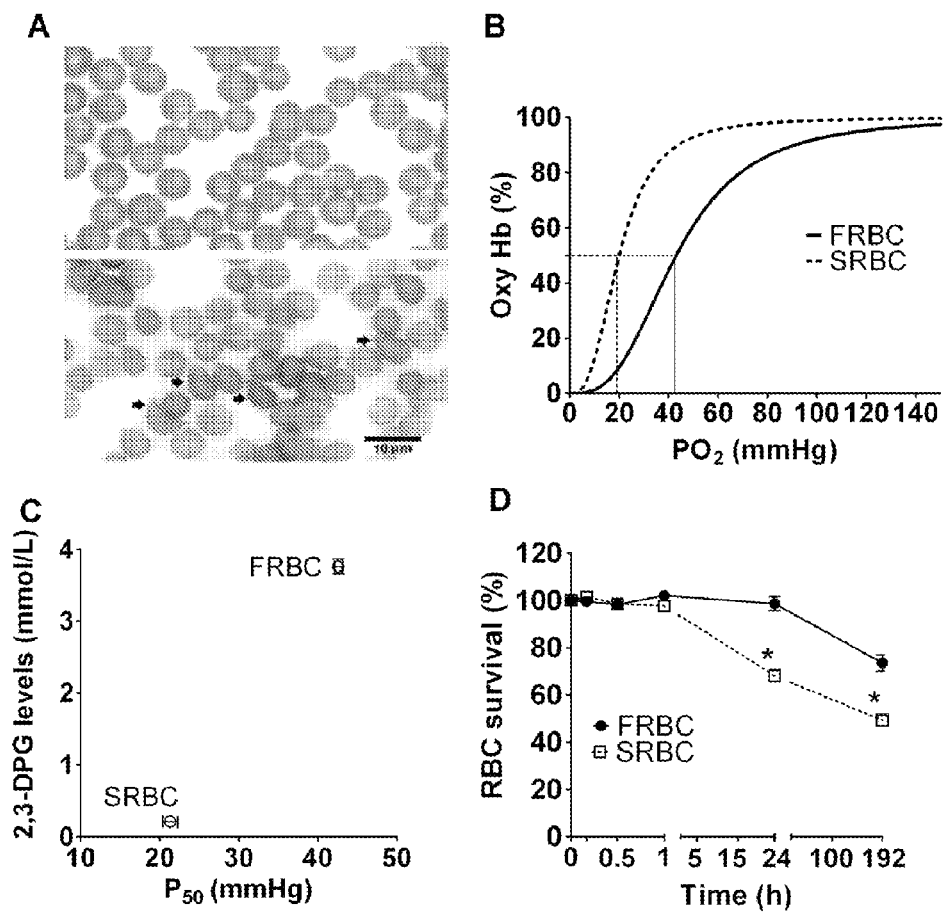
FIGS. 1A-1D depict storage-induced morphological, biochemical, and functional changes in murine RBCs in vitro. (A) Stained smears of fresh red blood cells (FRBC, upper panel) and stored red blood cells (SRBC, lower panel), arrowheads in the lower panel showing increased numbers of abnormally shaped RBC after 2-week storage. (B) Oxygen dissociation curve (ODC) of FRBC and SRBC. $P_{50}$, defined as the partial pressure of oxygen at which Hb is 50% saturated, was calculated from the ODC. The ODC of SRBC was left-shifted with a $P_{50}$ of 21±1 mmHg, in contrast the $P_{50}$ of FRBC was 43±0 mmHg. (C) Comparison of changes in 2,3-DPG levels of FRBC (n=5) and SRBC (n=5) with $P_{50}$ of FRBC (n=3) and SRBC (n=3). (D) FRBC (n=6) or SRBC (n=6) survival was determined by the percentage of GFP-labeled RBC measured 24 h after transfusion divided by the percentage of GFP-labeled RBC at time 0 in WT mice. FRBC, fresh red blood cells (≤24 h); SRBC, stored red blood cells (2-week). *P<0.01 differs vs FRBC.

Vasoconstriction and other adverse effects result from the administration of stored red blood cells to a mammal. The present invention provides compositions and methods for reducing or eliminating the occurrence of adverse effects following the administration of stored red blood cells. As detailed in the accompanying examples, oxidizing the supernatant of stored red blood cells by exposure to nitric oxide converts extracellular active ferrous hemoglobin to inactive ferric hemoglobin and eliminates the occurrence of vasoconstriction resulting from administration of the stored red blood cells.

Red Blood Cells

Red blood cells can be derived from an autologous or allogeneic donor and subsequently administered to a recipient. Storage of red blood cells results in an induction of vasoconstriction following administration of the stored blood to a recipient (Reynolds et al. (2007) *Proc. Natl. Acad. Sci.* 104:17058-62; Bennett-Guerrero et al. (2007) *Proc. Natl. Acad. Sci.* 104:17063-68). Human red blood cells can be stored for a variety of time periods (e.g., at least 1, 2, 3, 4, 5, 6, or 12 hours or at least 1, 2, 3, 4, 5, 6, 7, 14, 21, 28, 42 days, or longer) prior to infusion to a donor according to the methods described herein. Red blood cells can be administered as, e.g., whole blood or packed red blood cells.

Nitric Oxide

A suitable concentration of nitric oxide for use in treatment of a red blood sample can vary, e.g., from 20 ppm to 80 ppm, 200 ppm to 500 ppm, 500 ppm to 800 ppm, 2,800 ppm, 3,000 ppm, or higher, depending on factors such as the size of the red blood cell sample, the flow rate, the length of the nitric oxide exposure period, the degree of laminar flow versus mixing in the microporous gas dialyzer, and/or other factors that a treating physician may deem relevant. Pharmaceutical grade nitric oxide is available commercially (INOmax™, Ikaria, Inc., Clinton, N.J.).

Gaseous nitric oxide used in the treatment of a red blood cell sample can be administered from a source of stored, compressed nitric oxide gas. The source of nitric oxide can be 100% nitric oxide, or diluted with $N_2$ or any other inert gas (e.g., helium). The nitric oxide can be obtained and stored as a mixture free of any contaminating $O_2$ or higher oxides of nitrogen. If desired, purity of the nitric oxide may be demonstrated with chemiluminescence analysis. Chemiluminescence NO—$NO_x$ analyzers are commercially available (e.g., Model 14A, Thermo Environmental Instruments, Franklin, Mass.). The final concentration of nitric oxide in the mixture may be verified with a chemical or chemiluminescence technique (see, e.g., Fontijin et al., *Anal. Chem.* 42:575 (1970)). Alternatively, NO and $NO_2$ concentrations may be monitored by means of an electrochemical analyzer. Any impurities such as $NO_2$ can be scrubbed by exposure to NaOH solutions, baralyme, sodalime. As an additional control, the $FiO_2$ of the final gas mixture may also be assessed.

Administration of nitric oxide gas to a red blood cell sample can be accomplished, for example, by attaching a tank of compressed nitric oxide gas in $N_2$ (or an inert gas), and a second tank of nitrogen (or another inert gas), to a device designed to mix gas from two sources. By controlling the flow of gas from each source, the concentration of nitric oxide administered to the red blood cell sample can be maintained at an optimal level. Nitric oxide gas may also be mixed with room air, using a standard low-flow blender (e.g., BIRD BLENDER®, Palm Springs, Calif.).

Nitric oxide can be generated from $N_2$ and $O_2$ (i.e., air) by using an electric nitric oxide generator. Such a generator is described in Zapol, U.S. Pat. No. 5,396,882. $NO_2$ formation from such a device can be reduced by scavenging the gas mixture before exposing the blood sample to $NO_2$.

A gas delivery device for nitric oxide delivery to a red blood cell sample can contain a nitric oxide dosimeter to permit the monitoring of the total dose of nitric oxide to which the sample is exposed. By use of a dosimeter, a determination can be made of when a sample has received the required amount of nitric oxide so that administration of the nitric oxide can be tapered off or terminated. A dosimeter can integrate the concentration of nitric oxide in the therapeutic gas (as measured by a nitric oxide concentration meter) with the gas flow rate (as measured by a gas flow meter) to determine the total amount of nitric oxide to which the red blood cell sample is exposed.

A gas-permeable material can be used to allow gaseous nitric oxide to diffuse across it and contact the red blood cell sample. Examples of such materials include gas-permeable membranes such as those used in blood oxygenators (e.g., dimethylpolysiloxane or polyalkylsulfone), and microporous materials such as Gore-tex™ or Celgard™, which allow gas molecules such as nitric oxide to pass through its micropores to dissolve in liquid. Use of an exemplary oxygenator (Living Systems Instrumentation Inc., St. Albans, Vt.) is described in the accompanying examples. A section of the gas-permeable material can be configured with one face in contact with the red blood cell sample and a second face in contact with a source of nitric oxide, separating the red blood cells from the source of nitric oxide but permitting individual molecules of nitric oxide gas to pass through and diffuse into the sample. Nitric oxide can optionally be contacted with a red blood cell sample during the infusion process, whereby the red blood cell sample flows from a vessel in which it is contained, is exposed to nitric oxide by passing across the gas-permeable material (which allows for nitric oxide diffusion into red blood cell sample), and is ultimately administered to the recipient. Gas exchangers with secondary flows can be used (see, e.g., Zapol and Qvist, Artificial Lungs for Acute Respiratory Failure, New York, Academic Press, 1976)

Aqueous solutions containing nitric oxide can be prepared for delivery of nitric oxide to a red blood cell sample. The nitric oxide may be dissolved in a pharmaceutically acceptable carrier liquid prior to introduction into the red blood cell sample. Carrier liquids useful for this purpose include standard saline solutions, aliquots of the red blood cell sample, and liquids such as fluorocarbons or organic solvents in which nitric oxide exhibits a high level of solubility (Shaw and Vosper J. Chem. Soc. Faraday Trans. 1. 73:1239-1244, 1977; Young, Solubility Data Series 8:336-351, 1981), so that a large concentration of nitric oxide can be delivered in a small volume of carrier.

Nitric Oxide-Releasing Compounds

As an alternative to (or in addition to) use of nitric oxide, a nitric oxide-releasing compound can be exposed to a red blood cell sample according to the methods described herein. Nitric oxide-releasing compounds useful in the methods described herein include: nitroso or nitrosyl compounds (e.g., S-nitroso-N-acetylpenicillamine, S-nitroso-L-cysteine, and nitrosoguanidine) characterized by a nitric oxide moiety that is spontaneously released or otherwise transferred from the compound under physiological conditions; compounds in which nitric oxide is a ligand on a transition metal complex, and as such is readily released or transferred from the compound under physiological conditions (e.g., nitroprusside, nitric oxide-ferredoxin, or a nitric oxide-heme complex); and nitrogen-containing compounds that are metabolized by enzymes to produce the nitric oxide radical (e.g., arginine, glyceryl trinitrate, isoamyl nitrite, sodium nitrite, inorganic nitrite, azide, and hydroxylamine). Additional nitric oxide-releasing compounds include nitroglycerin and SIN-1.

The nitric oxide-releasing compound can be an ultra-short-acting nitric oxide-releasing compound such as 1-[2-(carboxylato)pyrrolidin-1-yl]diazen-1-ium-1,2-diolate ("PROLI/NO"), 1-hydroxy-2-oxo-3-(N-methyl-3-aminopropyl)-3-methyl-1-triazene ("NOC-7"; Zhang et al. (1996) Circulation 94:2235), a nitric oxide adduct of N,N'-dimethylhexanediamine ("DMHD/NO"; Kaul et al. (1997) J. Cardiovasc. Pharmacol. Ther. 1997 2(3):181), or (Z)-1-[N-Methyl-N-[6-(N-methylammoniohexyl)amino]]diazen-1-ium-1,2-diolate ("MAHMA/NO"). In some embodiments, the ultra-short-acting nitric oxide-releasing compound has a half-life of less than 90 minutes (or less than 60 minutes, less than 30 minutes, less than 20 minutes, less than 10 minutes, less than 5 minutes, less than 2 minutes, or less than 1 minute).

A compound known or believed to be a nitric oxide-releasing compound (e.g., an ultra-short-acting nitric oxide-releasing compound) can be directly tested for its efficacy by use of an animal model described herein. Alternatively, such a compound may first be screened for its ability to stimulate guanylate cyclase, the enzyme to which nitric oxide binds and thereby exerts its biological activity, in an in vitro assay such as is described by Ishii et al. (1991) Am. J. Physiol. 261:H598-H603.

The following are examples of the practice of the invention. They are not to be construed as limiting the scope of the invention in any way.

EXAMPLES

Example 1

Diabetes Augments and Nitric Oxide Prevents Adverse Hemodynamic Effects of Transfusing Syngeneic Stored Blood in Mice Animals All animal studies were approved by the Subcommittee on Research Animal Care at Massachusetts General Hospital, Boston, Mass., Eight- to ten-week-old male C57BL/6J wild-type (WT) mice and B6.Cg-m+/+Leprdb/J (C57BL/6J background) diabetic (db/db) mice were studies. Additional WT mice were fed a high-fat diet (60 kcal % fat; Research Diets, Inc., New Brunswick, N.J.) for 4-6 weeks (HFD-fed WT). Eight- to ten-week-old, male green fluorescent protein (GFP) transgenic C57BL/6-Tg (UBC-GFP) 30Scha/J (C57BL/6J background) mice with GFP expressed on erythrocytes were used to measure RBC survival. All mice were obtained from Jackson Laboratory (Bar Harbor, Me.).

Murine Blood Collection and Storage

Blood (~1 ml/mouse) was withdrawn aseptically by open chest cardiac puncture from C57BL/6J WT mice into a syringe containing CPDA-1 (Sigma-Aldrich, St. Louis, Mo.). The final concentration of CPDA-1 was 14%. After collection, blood was leukoreduced by passage through a neonatal leukoreduction filter (Pall Biomedical Products Co., East Hills, N.Y.). Efficacy of leukoreduction was measured by a complete blood count (HEMAVET® Veterinary Analyzer, Heska, Loveland, Colo.). Leukoreduced blood was centrifuged for 15 min at 600 g, adjusted to a hematocrit (Hct) of 70-75% by removing plasma, and stored in EPPENDORF® tubes at 4° C. The lipopolysaccharide (LPS) levels in samples of fresh leukoreduced murine RBC (FRBC) or stored leukoreduced murine RBC (SRBC) were measured using a limulus amoebocyte lysate assay (LAL) (see Novitsky et al. J Clin Microbiol 1985; 21: 211-6).

Preparation of Stored RBC Components

Supernatants were obtained after centrifuging FRBC or SRBC at 400 g for 10 min at 4° C. To minimize hemolysis induced by washing, FRBC and SRBC were gently washed with 10 volumes of 1.5% sodium chloride and centrifuged at 400 g for 10 min at 4° C. Prior to transfusion, washed FRBC or SRBC were resuspended in fresh murine plasma to obtain a final Hct of 70-75%.

To oxidize ferrous Hb in the supernatant of SRBC, the supernatant was exposed to 800 ppm nitric oxide gas in nitrogen through an oxygenator (Living Systems Instrumentation Inc., St. Albans, Vt.) for 2 h to produce metHb (Yu et al., Circulation 2008; 117: 1982-90). Supernatant (2 ml) was then dialyzed 3 times (SPECTRA/POR® molecular porous membrane MWCO: 12-14,000, Spectrum Laboratories Inc., Rancho Dominguez, Calif.) against 3 L of 0.9% saline to reduce low molecular weight nitric oxide metabolites.

Biochemical, Hematological, and Morphological Changes in Stored Murine RBCs

Blood gas tensions ($PCO_2$ and $PO_2$), pH, and standard base excess (SBE) were measured in FRBC and SRBC (ABL800 FLEX, Radiometer, Westlake, Ohio). Electrolyte concentrations (sodium, potassium, calcium, chloride, $HCO_3^-$), and lactate were also determined in FRBC and SRBC (Critical Care Xpress, Nova Biomedical, Waltham, Mass.).

To determine Hb levels in the supernatant, FRBC or SRBC were centrifuged at 1700 g for 8 min at 4° C., and supernatant Hb levels were measured with a QUANTICHROM™ Hb Assay Kit (BioAssaySystems, Hayward, Calif.). Hemolysis (%) was calculated using a standard formula: Hemolysis (%)=[supernatant Hb×(1−% Hct)]/total Hb×100 (see Kamel et al., Blood Transfus 2010; 8: 260-6).

To investigate the impact of storage on RBC morphology, FRBC or SRBC were smeared and stained with the HEMA3™ manual staining system (Fisher Diagnostics, Middletown, Va.), and images were obtained using a Nikon ECLIPSE® 80i upright microscope fitted with a Plan Fluor 60× dry objective (Nikon Instruments Inc., Melville, N.Y.).

Oxygen dissociation curves (ODC) of FRBC and SRBC (adding 20 µl of RBC to 5 ml Hemox-solution containing 20 µl of additive-A and 10 µl of anti-foaming agent) were determined with a Hemox-analyzer (TCS Scientific Corp., New Hope, Pa.). P50, defined as the partial pressure of oxygen at which Hb is 50% saturated, was calculated from the ODC. The levels of 2,3-DPG in FRBC and SRBC were measured using a 2,3-DPG kit (Roche Diagnostics, Mannheim, Germany).

Measuring Murine RBC Survival

The GFP-labeled RBC method reported by Gilson et al. (Gilson et al., Transfusion 2009; 49: 1546-53) was used to measure survival of transfused murine RBCs. Briefly, blood was withdrawn from both UBC-GFP and WT mice by cardiac puncture into a 1 ml syringe containing CPDA-1, and blood mixtures were prepared containing 40% RBCs from UBC-GFP mice and 60% RBCs from WT mice, leukoreduced, centrifuged, and stored at 4° C. for <24 h (FRBC) and 2 weeks (SRBC). WT mice were transfused with 100 µL of FRBC or SRBC containing GFP-labeled RBCs via a tail vein. At 10 min, 30 min, 1 h, 24 h, and 8 d after transfusion, blood samples were obtained from the retro-orbital space into heparinized glass microcapillary tubes. The percentage of GFP-positive RBCs was determined by forward scatter/side scatter (FSC/SSC) on a 5 Laser LSR FORTESSA™ (BD Biosciences, San Jose, Calif.). The flow cytometer was calibrated to the same settings on different acquisition days by SPHERO™ rainbow fluorescent particles (Spherotech Inc., Lake Forest, Ill.). The RBC survival rate at 24 h after transfusion (%) was calculated by dividing the percent of GFP-positive RBC measured 24 h after transfusion by the percent of GFP-positive RBC at time 0. Fluorescence at time 0 was extrapolated by linear regression from the data at 10 min, 30 min, and 1 h.

Biochemical Assays 2 h after Transfusion

After transfusion of FRBC or SRBC, mice were sacrificed at 2 h with an intraperitoneal injection of pentobarbital (200 mg/kg). Approximately 1 ml of blood was withdrawn from each mouse by cardiac puncture into a heparinized syringe and centrifuged at 4000 rpm, 4° C. for 8 min. Heparinized plasma was obtained to measure blood chemistry, as well as interleukin-6 (IL-6), haptoglobin (Hp), and hemopexin (Hx) levels. Serum samples were obtained for the measurement of iron levels. Liver specimens were snap-frozen in liquid nitrogen for subsequent determination of heme oxygenase-1 (HO-1).

To compare the acute biochemical effects of transfusing FRBC or SRBC, 12 WT and 12 db/db mice were sacrificed at 10 min post-transfusion with an intraperitoneal injection of pentobarbital (200 mg/kg). Whole blood was obtained by cardiac puncture for blood chemistry measurements.

Measurement of Serum Iron Levels

Serum iron levels were determined using an Iron/Unsaturated Iron Binding Capacity Assay (Thermo Fisher Scientific, Middletown, Va.).

Measurement of Plasma IL-6, Hp, and Hx Levels

Plasma IL-6 levels were determined with a DUOSET® mouse IL-6 Elisa Kit (R&D Systems, Minneapolis, Minn.). Plasma Hp and Hx levels were measured using mouse Hp and Hx Elisa kits, respectively (Life Diagnostics, Inc., West Chester, Pa.).

Quant Quantification of Tissue mRNA Levels

Total mRNA was extracted from murine livers using TRIZOL® reagent (Invitrogen Life Technologies, Carlsbad, Calif.). cDNA was synthesized by the reverse transcriptase reaction (MMLV-RT, Invitrogen Life Technologies, Carlsbad, Calif.). Real-time amplification of transcripts was performed by the SYBR® method using an EPPENDORF MASTERCYCLER® Realplex (Eppendorf, Hamburg, Germany). The relative expression of target transcripts was normalized to the levels of 18S rRNA and analyzed using the relative CT method.

Non-Invasive Measurement of Blood Pressure in Awake WT, HFD-Fed WT and db/db Mice after Transfusion of FRBC or SBRC FRBC, SRBC, washed FRBC and SRBC, supernatants from FRBC and SRBC, and oxidized supernatant from SRBC were transfused (total injectate volume was 10% of estimated blood volume) via a tail vein into WT, HFD-fed WT, or db/db mice. Systolic blood pressure was measured with a non-invasive blood pressure system (XBP 1000, Kent Scientific, Torrington, Conn.) (Yu et al., Circulation 2008; 117: 1982-90; Yu et al., Anesthesiology 2010; 112: 586-94). All tail vein injections were performed over one minute. One group of db/db mice received SRBC while breathing 80 ppm nitric oxide in air (Medical-Technical Gases, Inc., Medford, Mass.) from 10 min prior to transfusion until 2 h after transfusion using methods described in Yu et al., Circulation 2008; 117: 1982-90.

Invasive Hemodynamic Measurements in Anesthetized Mice

Invasive hemodynamic measurements were performed as described in Yu et al., Anesthesiology 2010; 112: 586-94. Left ventricular pressure-volume loops and cardiac output (CO), as well as mean arterial blood pressures (MAP), were measured at baseline and 5 min after transfusion with FRBC, SRBC, the supernatant from FRBC, or the supernatant from SRBC (10% of estimated blood volume, infused at a rate of 75 µL/min over 3 min through a separate catheter placed in the right jugular vein).

Statistical Analysis

All values are expressed as mean±SEM. Data were analyzed by a one-way ANOVA with Tukey adjustment (SigmaStat 3.0.1; Systat Software, Inc., San Jose, Calif.). Systolic blood pressure measurements in awake mice were analyzed by a repeated measures two-way ANOVA with interaction. Probability values less than 0.05 were considered significant.

Characterization of Stored Murine Blood

FRBC stored for ≤24 h were compared with SRBC stored for 2 weeks. In SRBC, pH, $PO_2$, $HCO_3^-$, and SBE were markedly decreased while $PCO_2$, and lactate were greater than in FRBC (Table 1). In addition, sodium levels were less and potassium levels were greater in SRBC than in FRBC. The level of hemolysis in SRBC was markedly greater than that in FRBC. Similarly, supernatant Hb levels were greater in SRBC than in FRBC. MetHb levels measured in the supernatant of both FRBC and SRBC were less than 1% of the supernatant Hb.

TABLE 1

Comparison of blood chemistry in FRBC (≤24 h) and SRBC (2 weeks)

| | FRBC (n = 5) | SRBC (n = 5) |
|---|---|---|
| pH | 7.06 ± 0.03 | 6.53 ± 0.03* |
| $PCO_2$ (mmHg) | 16 ± 1 | 35 ± 4* |
| $PO_2$ (mmHg) | 217 ± 9 | 140 ± 12* |
| $HCO_3^-$ (mmol/L) | 4 ± 0 | 3 ± 0* |
| SBE (mmol/L) | −24 ± 0 | −30 ± 1* |
| $Na^+$ (mmol/L) | 152 ± 0 | 137 ± 1* |
| $K^+$ (mmol/L) | 3.7 ± 0.4 | 34.4 ± 2.6* |
| $Cl^-$ (mmol/L) | 121 ± 1 | 120 ± 1 |
| $Ca^{++}$ (mmol/L) | 0.06 ± 0 | 0.05 ± 0 |
| Lactate (mmol/L) | 2.2 ± 0.3 | 18.3 ± 2.0* |
| Hb (g/dl) | 14.1 ± 1.6 | 12.9 ± 0.2 |
| Supernatant Hb (mg/dl) | 64 ± 6 | 571 ± 51* |
| Hemolysis (%) | 0.1 ± 0 | 0.8 ± 0* |

Values are mean ± SEM. FRBC, fresh red blood cells; SRBC, stored red blood cells; SBE, standard base excess; Hb, hemoglobin.
*P < 0.01 differs vs FRBC In FRBC, cell morphology was dominated by discocytes (FIG. 1A, upper panel). After storage for 2 weeks, the majority of RBCs were abnormally shaped (e.g., echinocytes or spheroechinocytes, as indicated by arrows in FIG. 1A, lower panel). Storage-induced morphological changes were observed in murine RBCs that appear similar to those reported in stored human RBCs (Makley et al., Shock 2010; 34: 40-5).

The primary function of the RBC is to transport oxygen; thus, changes of Hb-oxygen affinity after RBC storage were measured. The ODC of SRBC was markedly left-shifted, as compared to FRBC (21±1 versus 43±0 mmHg, respectively; FIG. 1B, n=5, P<0.01). Erythrocyte 2,3-DPG levels decreased from 3.8±0.1 mmol/L in FRBC to 0.2±0.1 mmol/L in SRBC (FIG. 1C). Since oxygen affinity is modulated by the allosteric inhibitory binding effects of 2,3-DPG to Hb in mice, the reduction of 2,3-DPG with storage, similar to that observed in stored human RBC, markedly augmented the oxygen affinity. These results demonstrate that murine RBCs undergo biochemical, hematological, and morphological changes during the 2-week storage.

Impact of Storage Duration on RBC Survival after Syngeneic Transfusion

To track the survival of infused FRBC and SRBC, the impact of storage on GFP-labeled RBCs was studied. Twenty-four hours after transfusing GFP-labeled FRBC, the fraction of GFP-labeled erythrocytes was 99±3% of that calculated at time 0 after infusion (FIG. 1D). Twenty-four hours after transfusing GFP-labeled SRBC, the fraction of GFP-labeled erythrocytes was 68±1% of that calculated at time 0 after transfusion (FIG. 1D). Beginning 24 h after transfusion, the rate of decrease in GFP-labeled erythrocytes was similar in FRBC and SRBC. These results are consistent with those reported by Gilson and colleagues (Gilson et al., Transfusion 2009:49: 1546-53) and suggest that storage lesion seen in stored blood has a heterogeneous impact on erythrocytes.

Impact of FRBC and SRBC Transfusion on Hct, Hb and Plasma Hb in WT, HFD-Fed WT, and db/db Mice Arterial blood samples were drawn from mice at 10 min (WT and db/db mice) and 2 h (WT, HFD-fed WT, and db/db mice) after transfusion of FRBC or SRBC. Transfusion of either FRBC or SRBC increased Hct and total Hb levels at 10 min and 2 h after transfusion in all studied mice. Transfusion with SRBC, but not FRBC, increased plasma Hb levels at 10 min and 2 h after transfusion in all groups of mice studied. These results indicate that increased plasma Hb levels after SRBC transfusion is most likely due to the release of Hb during storage and after transfusion.

Serum Iron Levels after Transfusion

Figure 2:
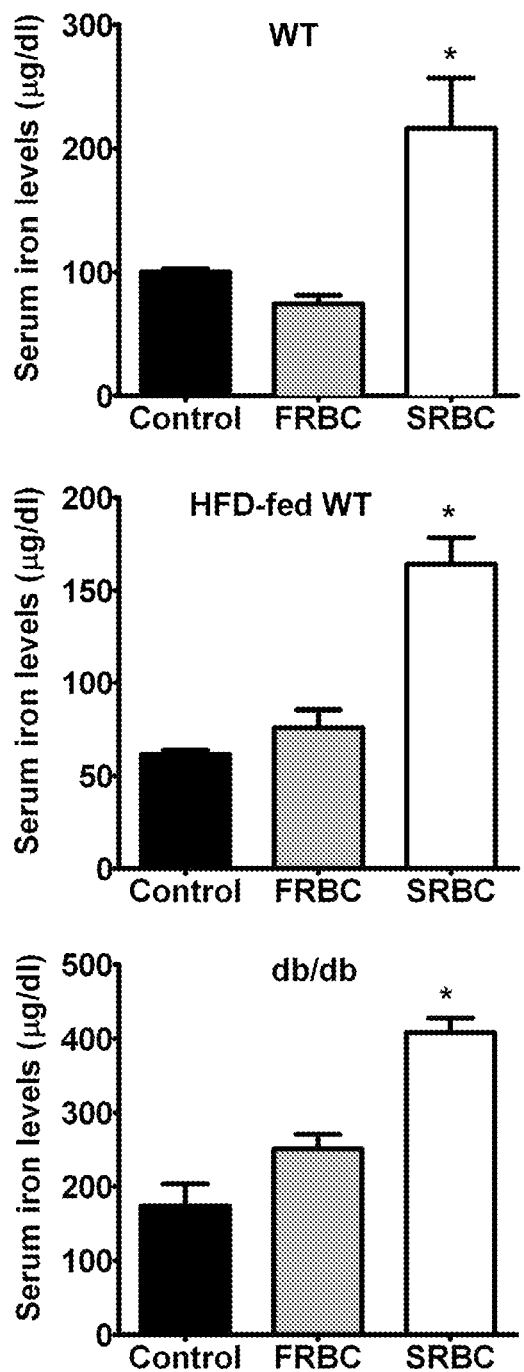
FIGS. 2A-2C are graphs depicting serum iron levels 2 h after transfusion with FRBC or SRBC in awake WT (A), HFD-fed WT (B) and db/db (C) mice. Control, no transfusion (n=4/group); FRBC, transfusion with FRBC (n=6/group); SRBC, transfusion with SRBC (n=6/group). *P<0.05 differs vs control and FRBC.

Since SRBC have a shortened lifespan and are rapidly removed from the circulation, they could contribute iron from their heme to enhance the reactive oxygen species generation. Serum iron levels were measured in mice at 2 h after transfusion of FRBC or SRBC (FIG. 2). Serum iron levels were greater at 2 h after transfusion of SRBC into WT, HFD-fed WT, and db/db mice, but not after transfusion of FRBC. These results demonstrate that transfusion of SRBC increases serum iron more than FRBC transfusion.

Inflammation after Transfusion

Figure 3:
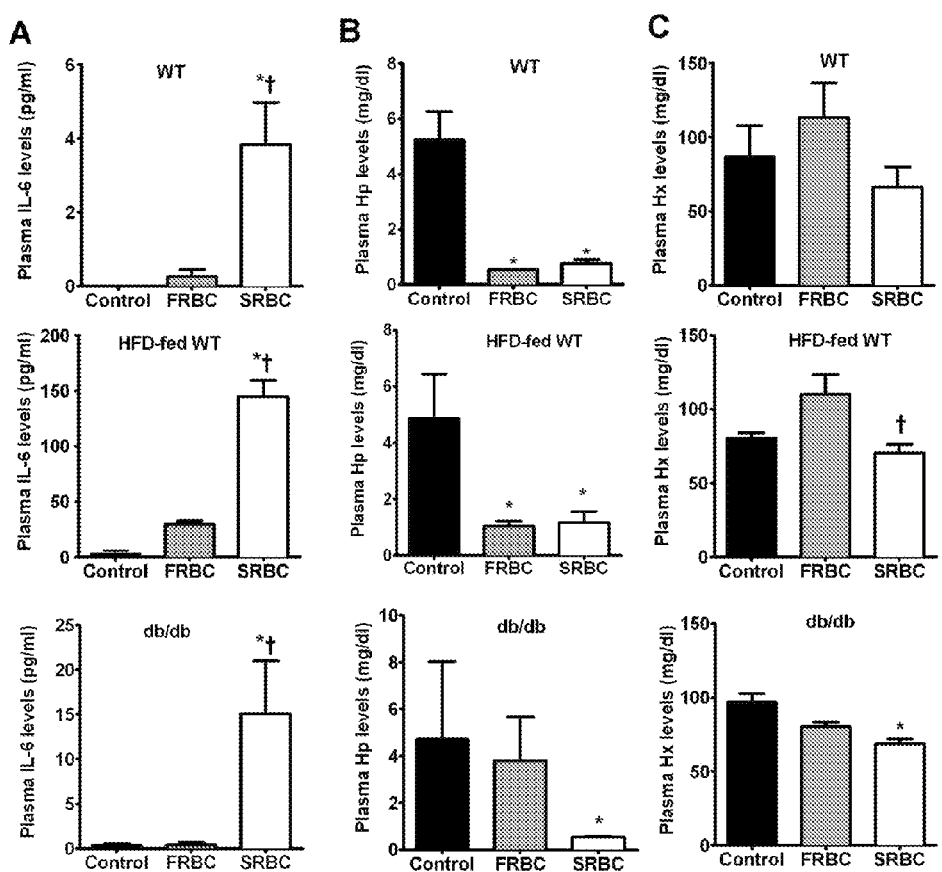
FIGS. 3A-3C are graphs depicting plasma levels of IL-6 (A), Hp (B), and Hx (C) at 2 h after transfusion of FRBC or SRBC in awake WT, HFD-fed WT and db/db mice. Control, no transfusion (n=4/group); FRBC, transfusion with fresh RBC (n=6/group); SRBC, transfusion with stored RBC (n=6/group). *P<0.05 differs vs control; †P<0.01 differs vs FRBC.

To learn whether transfusion of either FRBC or SRBC would induce a systemic inflammatory response in mice, IL-6 levels were measured in plasma samples collected from WT, HFD-fed WT, and db/db mice at 2 h after transfusion (FIG. 3A). Transfusion of SRBC, but not FRBC, increased plasma IL-6 levels in WT, HFD-fed WT, and db/db mice (P<0.05). Since approximately 97% of the white blood cells (WBC) in stored cells were removed by leukoreduction and no endotoxin (e.g., LPS) was detected in the transfused samples, the increased IL-6 level is most likely a result of SRBC transfusion.

Plasma Hp, Hx and Hepatic HO-1 after Transfusion

The primary protective mechanisms against extracellular Hb are often termed "antioxidant proteins", such as Hp, Hx and HO-1. Extracellular Hb binds to circulating Hp. Clearance of the Hb-Hp complex takes place within the circulation and the liver (macrophages), eventually leading to the breakdown of heme via HO-1 (Buehler et al., Antioxid Redox Signal 2010; 14: 1713-28). Hx serves as the primary carrier of plasma heme and participates in its clearance by transporting it to the liver (Gutteridge et al., Biochem J 1988; 256: 861-5). HO-1 is the inducible isoform of heme degradation and is protective against inflammatory injury (Immenschuh et al., Curr Drug Targets 2010; 11: 1541-50).

Figure 4:
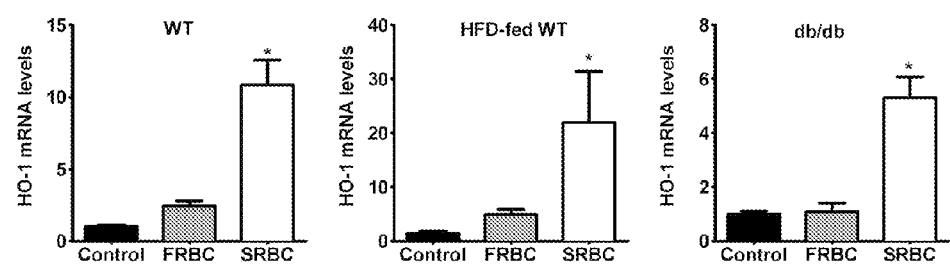
FIGS. 4A-4C are graphs depicting changes of hepatic HO-1 mRNA levels at 2 h after transfusion of FRBC or SRBC in awake WT (A), HFD-fed WT (B) and db/db (C) mice. Control, no transfusion (n=4/group); FRBC, transfusion of fresh RBC (n=6/group); SRBC, transfusion of stored RBC (n=6/group). *P<0.05 differs vs control and FRBC.

After measuring increased levels of plasma Hb after SRBC transfusion, the impact of FRBC and SRBC transfusion on the mechanisms responsible for clearing plasma Hb was examined. Plasma Hp levels decreased at 2 h after either FRBC or SRBC transfusion (FIG. 3B). Transfusion of SRBC decreased plasma Hx levels at 2 h in HFD-fed WT and db/db mice, but not in WT mice (FIG. 3C). Transfusion of FRBC did not change Hx levels. At 2 h after transfusion, hepatic HO-1 mRNA levels were greater in WT, HFD-fed WT, and db/db mice after SRBC transfusion, but not after FRBC transfusion (FIG. 4, P<0.05). These results suggest that since Hp levels at baseline are quite low in the mouse, the small amounts of Hb released in response to FRBC transfusion are sufficient to markedly reduce Hp levels, whereas the Hx levels are higher and were only modestly reduced at 2 h after transfusion. Transfusion of SRBC induced hepatic HO-1 mRNA levels due to increased heme released from SRBC.

Hemodynamic Effects of Transfusing FRBC and SRBC

Figure 5:
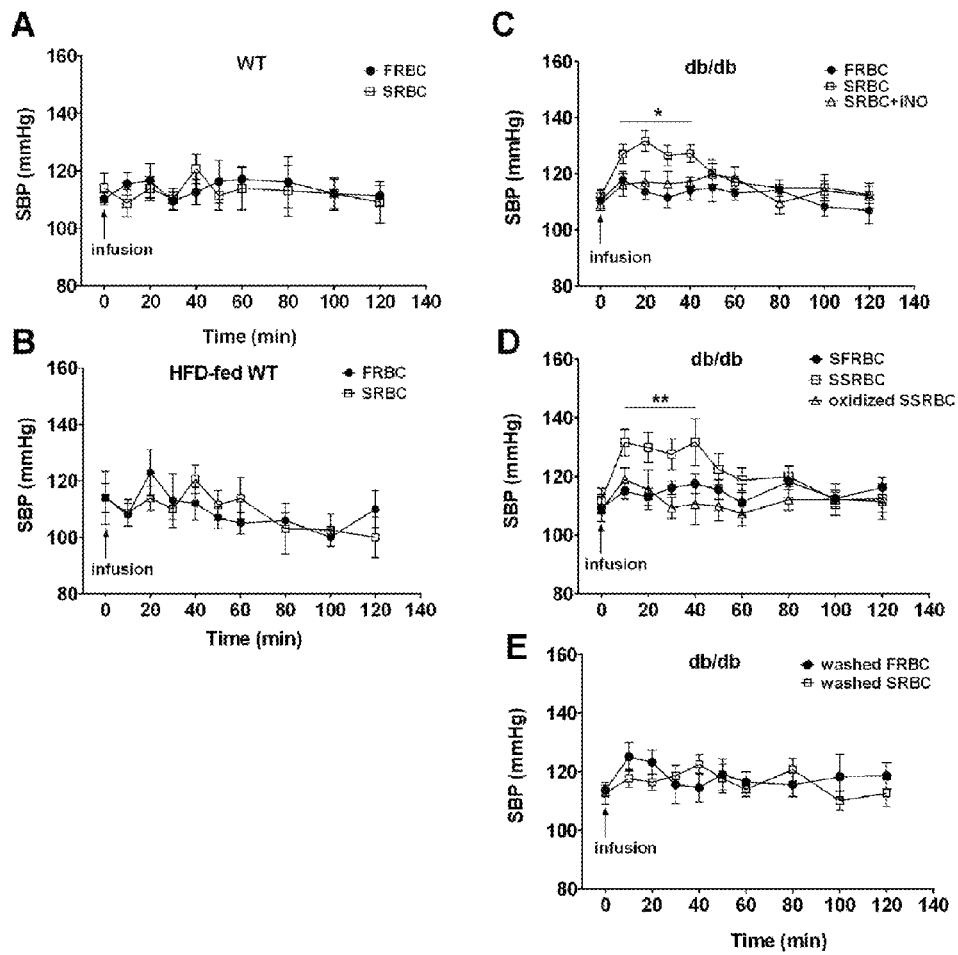
FIGS. 5A-5E are graphs depicting systemic blood pressure (SBP, mmHg) after different types of transfusions (10% estimated blood volume awake WT, HFD-fed WT, or db/db mice. (A) Transfusion with FRBC (n=5) or SRBC (n=6) in awake WT mice, (B) Transfusion with FRBC (n=6) SRBC (n=6) in awake HFD-fed WT mice. (C) Transfusion with FRBC (n=9) or SRBC with (n=12) or without (n=9) breathing nitric oxide (iNO, 80 ppm) in awake db/db mice, (D) Transfusion with supernatant from FRBC (STREW, n=11), supernatant from SRBC (SSRBC, n=7), or oxidized SSRBC (n=6) in awake db/db mice, (E) Transfusion with washed FRBC (n=9) or washed SRBC (n=6) in awake db/db mice. FRBC, fresh red blood cells; SRBC, stored red blood cells. *P<0.05 differs vs FRBC and SRBC+iNO.

Transfusing a blood substitute containing less than 1% of tetrameric Hb can produce systemic vasoconstrictor effects (Yu et al., Anesthesiology 2010; 112: 586-94). To examine the effects of transfusing FRBC and SRBC on systolic blood pressure, FRBC or SRBC (as a 10% of blood volume injection) were administered via a tail vein in awake mice. Transfusion of either FRBC or SRBC did not change systolic blood pressure in awake WT mice (FIG. 5A). Mice with endothelial dysfunction (e.g. HFD-fed WT or db/db mice) are more sensitive to the vasoconstrictor effects of tetrameric Hb (see Yu et al., Anesthesiology 2010; 112: 586-94). In awake HFD-fed WT mice, transfusion of FRBC or SRBC did not change systolic blood pressure (FIG. 5B). In contrast, transfusion of SRBC, but not FRBC, increased systolic blood pressure in awake db/db mice (from 111±2 mmHg at baseline to 127±3 mmHg at 10 min, P<0.05, FIG. 5C). Since nitric oxide breathing prevented the systemic vasoconstriction induced by infusing tetrameric Hb in mice (Yu et al., Circulation 2008; 117: 1982-90), the ability of inhaled nitric oxide to prevent the vasoconstricting effects of transfusing db/db mice with SRBC was studied. Breathing 80 ppm nitric oxide beginning 10 min prior to transfusion and continuing for 2 h thereafter completely prevented the systemic hypertension induced by the transfusion of SRBC into db/db mice (FIG. 5C).

To investigate which component of SRBC is responsible for its vasoconstricting effects, the supernatant obtained from SRBC or washed SRBC was transfused into awake db/db mice. Transfusing the supernatant of SRBC (10% of estimated blood volume of db/db mouse38 or 250 μL, equivalent to 4 times the volume of supernatant given by transfusing 250 μL of SRBC) increased systemic blood pressure (from 112±4 to 132±4 mmHg, P<0.05), which lasted for 40 min (FIGS. 5D and 5E).

To minimize hemolysis induced by washing, SRBC were suspended in 1.5 g % sodium chloride. The transfusion of washed SRBC into db/db mice did not increase systemic blood pressure (FIG. 5E).

Figure 6:
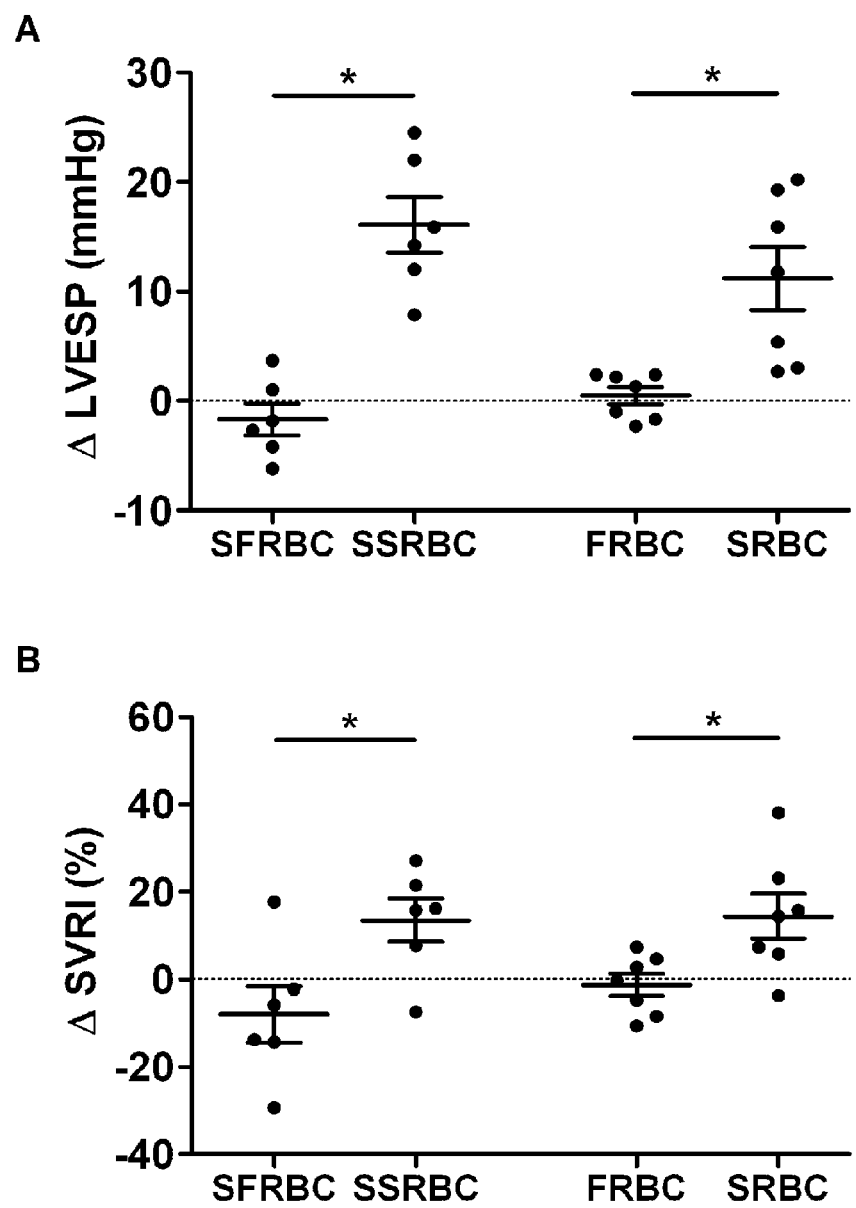
FIGS. 6A-6B are graphs depicting comparison of changes in systemic hemodynamic measurements in anesthetized db/db mice before and after transfusion of supernatant of FRBC (SFRBC, n=6), supernatant of SRBC (SSRBC, n=6), FRBC (n=7) or SRBC (n=7). (A) Changes in LVESP (mmHg) before and 10 min after transfusion. (B) Changes in SVRI (%) before and 10 min after transfusion. LVESP, left ventricular end-systolic pressure; SVRI, systemic vascular resistance index *P<0.05 differs vs either supernatant of FRBC or FRBC group.

Invasive hemodynamic measurements obtained in anesthetized db/db mice confirmed the findings in awake db/db mice. Transfusion of SRBC or supernatant from SRBC increased left ventricular (LV) end-systolic pressure (LVESP, FIG. 6A) and systemic vascular resistance index (SVRI, FIG. 6B), whereas transfusion of FRBC or supernatant from FRBC did not alter these hemodynamic parameters. After the supernatant obtained from SRBC was oxidized by exposure to nitric oxide gas (thereby converting ferrous Hb to ferric Hb) with subsequent dialysis to remove low molecular weight components (e.g., nitrite and nitrate), transfusion into awake db/db mice did not increase their systemic blood pressure (FIG. 5D). These hemodynamic results suggest that infusion of the supernatant from SRBC causes systemic vasoconstriction, which is most likely due to the infusion of supernatant Hb released during 2 weeks of storage (Donadee et al., Circulation 2011; 124: 465-76; Yu et al., Anesthesiology 2010; 112: 586-94).

Example 2

Pulmonary Hypertension in Lambs Transfused with Stored Blood

Processing or Blood Products

All experiments were approved by the Subcommittee on Research Animal Care, Massachusetts General Hospital, Boston, Mass. Thirty-six 3- to 4-month-old Polypay lambs (New England Ovis, Dover, N.H.) weighing 32±2 kg were studied (Hulet et al., J Anim Sci 1984; 58:15-24). Following an intramuscular injection of ketamine HCl (15 mg/kg; Hospira, Inc., Lake Forest, Ill.), blood (450 ml) was drawn from an external jugular vein into a Double Blood-Pack Unit (Fenwal, Inc., Lake Zurich, Ill.) containing citrate-phosphate-dextrose solution. Blood was then leukoreduced at room temperature, using an integrated RS2000 leukoreduction filter. Erythrocytes were separated from plasma by centrifugation (600 g for 10 min at 24° C.) and stored for either 2 or 40 days at 4° C. in an additive solution (110 ml) containing saline, adenine, glucose and mannitol (AS-1, Adsol Solution, Fenwal, Inc.).

Biotinylation of Ovine Erythrocytes

In vivo survival of transfused packed erythrocytes (PRBCs) was measured in 8 lambs using a modified version of the methods of Mock et al., Transfusion 1999; 39:156-6. After storage in AS-1 for either 2 (n=4) or 40 days (n=4), PRBCs (60 ml) were withdrawn from the blood storage bag and separated from supernatant by centrifugation at 600 g for 15 min at 4° C. Supernatant was stored at 4° C. The pelleted PRBCs were resuspended in washing solution (60 ml; sodium chloride 0.87%, sodium bicarbonate 0.2%, dextrose 0.2%, and sodium phosphates 0.1%; Hospira, Inc.). Centrifugation was repeated, and the supernatant was discarded. Washed PRBCs were resuspended in washing solution (60 ml) containing sulfo-N-hydroxysuccinimide-biotin (10 μg/ml; Thermo Fisher Scientific, Rockford, Ill.) and incubated at room temperature for 40 min. To remove unbound sulfo-N-hydroxysuccinimide-biotin, PRBC were washed twice with washing solution, as described above. After the final washing step, PRBC were resuspended in the previously stored supernatant.

Biotinylated PRBCs were transfused into sheep donors via a 16-G Angiocath (BD Infusion Therapy Systems, Inc., Sandy, Utah) placed in an external jugular vein. Venous blood samples were drawn into heparinized 4-ml Vacutainers (BD, Franklin Lakes, N.J.) at 15 min, 30 min, 60 min, 24 h, and 7 days later.

To assess the survival of biotinylated PRBC, blood samples (50 μl) were incubated for 20 min at room temperature with fluorescein isothiocyanate-tagged streptavidin (250 μl of washing solution containing 20 μg/ml streptavidin-fluorescein isothiocyanate; Biolegend, San Diego, Calif.). Fluorescein isothiocyanate-labeled PRBC were detected in forward versus side scatter (FSC/SSC) on a LSRFortessa flow cytometer (BD Biosciences, San Jose, Calif.). Sphero rainbow fluorescent particles (3.0-3.4 μm; Spherotech, Inc., Lake Forest, Ill.) were used to calibrate settings of the flow cytometer on different acquisition days. An extrapolation of the number of biotinylated PRBC at 0 h was performed and equated to 100%. Of 100,000 total events, the ratio of the percentage of biotinylated cells in blood samples obtained after the transfusion to the percentage of biotinylated cells calculated to be present at 0 h was calculated.

Animal Preparation and Hemodynamic Monitoring

Invasive hemodynamic measurements were performed in 28 lambs. Anesthesia was induced by breathing 5% isoflurane (Baxter, Deerfield, Ill.) in oxygen via mask. After endotracheal intubation, animals underwent a tracheostomy and were instrumented with indwelling carotid artery and pulmonary artery catheters, as previously described (Yu et al., Anesthesiology 2010; 112:586-94). After a 2-h recovery period from general anesthesia in a large-animal restraint unit (Lomir, Malone, N.Y.), the mean arterial pressure (MAP), mean pulmonary arterial pressure (PAP), and central venous pressure were monitored continuously using a Gould 6600 amplifier system (Gould Electronics, Inc., Eastlake, Ohio). Pulmonary capillary wedge pressure (PCWP) and heart rate were intermittently measured every 10-30 min. Cardiac output was assessed by thermal dilution as the average of three measurements after intravenous bolus-injection of 10 ml ice-cold saline solution. Systemic vascular resistance index and pulmonary vascular resistance index (PVRI), as well as cardiac index, were calculated using standard formulae. Hemodynamic data was collected until 4 h after the end of transfusion.

Hemodynamic Effects of Stored PRBC Transfusion in Awake Lambs

Six groups of awake lambs were studied. All animals received an autologous transfusion of PRBCs, equivalent to 14% of their respective total blood volume, assuming 6.5% of body weight was blood volume (Hansard et al., Proc Soc Exp Blot Med 1956; 91:31-4). PRBCs were warmed to 37° C. and transfused over 30 min while the lambs breathed spontaneously via a tracheostomy at inspired oxygen fraction ($FiO_2$) 0.25. One group (n=5) of lambs received PRBCs, which were processed and stored for 2 days prior to transfusion (fresh PRBCs). A second group of lambs (n=6) was transfused with PRBCs that were stored for 40 days before transfusion (stored PRBCs). A third group (n=4) of lambs breathed 80 ppm nitric oxide (Medical-Technical Gases, Medford, Mass.) at 0.25 $FiO_2$ during transfusion with stored PRBCs. Nitric oxide breathing was continued for 30 min after the transfusion ended.

Hemodynamic Effects of Transfusing Stored PRBC in a Lamb Model of Endothelial Dysfunction Three additional groups of lambs were studied after intravenous infusion of the NOS inhibitor, $N^G$-nitro-L-arginine methyl-ester (L-NAME, Sigma-Aldrich, St. Louis, Mo.). A bolus of 25 mg/kg L-NAME was injected IV 1 h before transfusion (Weimann et al., Anesthesiology 2000; 92:1702-12). Concomitantly, an infusion of 5 mg/kg/h L-NAME was started and continued throughout the study. Partial inhibition of nitric oxide production was confirmed before, as well as 45 min and 5 h after commencing L-NAME administration by assessing the systemic vasodilation induced by an intravenous bolus injection of acetylcholine (Sigma-Aldrich). NOS-independent systemic vasodilation was also assessed by intravenous injection of sodium nitroprusside (Sigma-Aldrich) at the end of each experiment.

After L-NAME treatment, a fourth group of lambs (n=4) received fresh PRBCs, and a fifth group (n=5) received stored PRBCs. In the sixth group (n=4), following L-NAME injection, inhalation of 80 ppm nitric oxide at $FiO_2$ 0.25 was commenced 10 min prior to transfusion of stored PRBC. Nitric oxide breathing continued throughout the transfusion and for 30 min after transfusion ended.

Biochemical Analysis of Blood Samples

Arterial and venous blood samples (10 ml) were drawn immediately before transfusion, as well as 30 min, 2 h and 4 h after ending transfusion. Samples (10 ml) from the transfusion storage bags were obtained and processed immediately after transfusion in order to avoid bacterial contamination. Blood gas tensions and pH were analyzed using an ABL800 Flex blood gas analyzer (Radiometer Medical, Copenhagen, Denmark).

Cell-free hemoglobin levels in plasma and supernatant were measured using a QuantiChrom hemoglobin assay kit (BioAssay Systems, Hayward, Calif.). Hematocrit was measured by centrifugation of whole blood at 400 g for 10 min in capillary tubes (Fisher Scientific, Pittsburgh, Pa.). Hemolysis (in percent) was calculated from the following formula: Cell-free Hemoglobin [g/dl]·(100−Hematocrit [%])/Total Hemoglobin [g/dl].

Plasma and supernatant concentrations of nitrate and nitrite were measured with a Nitrate/Nitrite fluorometric assay kit (Cayman Chemical Company, Ann Arbor, Mich.). Plasma thromboxane $B_2$ ($TXB_2$) levels were determined with an EIA kit (Cayman Chemical Company). The levels of 2,3-diphosphoglycerate (2,3-DPG) were measured with a kit from Roche Diagnostics (Mannheim, Germany). Plasma interleukin-6 (IL-6) levels were measured with a bovine kit from Thermo Fisher Scientific. Haptoglobin (Hp) concentrations were assessed using a bovine Hp ELISA kit (Immunology Consultants Lab, Inc., Newberg, Oreg.).

The oxygen dissociation curve of leukoreduced blood stored for either 2 or 40 days was determined using a Hemox-analyzer (TSC Scientific Corp., New Hope, Pa.). The oxygen tension at which hemoglobin is half saturated ($P_{50}$) was calculated from the oxygen dissociation curve.

Quantitation of Messenger RNA (mRNA) Levels

At 4 h after transfusion, animals were euthanized by intravenous injection of 50 ml of 20% potassium chloride solution during isoflurane anesthesia. Tissue samples were obtained from the lung and liver, snap frozen in liquid nitrogen, and stored at −80° C. until further analysis.

RNA was extracted from tissues using Trizol (Invitrogen, Carlsbad, Calif.), and complementary DNA was synthesized using MMLV-RT (Invitrogen). Real-time amplification of transcripts was detected using a Mastercycler ep Realplex (Eppendorf, Hamburg, Germany). The relative expression of target transcripts was normalized to levels of 18S regulatory RNA. Primer pairs were used to detect transcripts encoding IL-6, CAGAAAATAAGCTGAAACTTCCA, ATGTCAGTGTGTGTGGCTGGAG; tumor necrosis factor-α, GGCTCTCCTGTCTCCCGT, GTTGGCTACAACGTGGGC; and myeloperoxidase, GCTGAGGCGGGACACAACCC, CCCAGTTCCGTTTCCGGGGC.

Statistical Analysis

All data are expressed as mean±SD. Statistical analysis was performed using GraphPad Prism 5 software (GraphPad Software, Inc., La Jolla, Calif.). For comparisons of fresh and stored PRBC after AS-1-storage, PRBC-survival experiments, and comparisons of mRNA levels a two-tailed, two-sample, independent t-test was applied to compare differences between two groups, and corrected for multiple comparisons using a Bonferroni adjustment. For hemodynamic experiments, a two-way ANOVA with repeated measures was used to compare differences between groups at various time points. However, when the interaction P value between time and condition was significant, comparisons were made at each individual time point using a one-way ANOVA with post-hoc Bonferroni-adjusted comparison testing. Within-group comparisons were performed using a two-tailed paired t-test. P values <0.05 were considered significant.

Chemical Properties of Leukoreduced and AS-1-Stored Lamb PRBCs

The chemical characteristics of leukoreduced PRBCs and their supernatants were analyzed after storage in AS-1 for either 2 or 40 days. Cell-free hemoglobin concentrations in the supernatant of fresh PRBCs were 41±13 mg/dl, resulting in a calculated level of hemolysis of 0.10±0.04%. In stored PRBC supernatant, cell-free hemoglobin concentrations and hemolysis levels were higher than in fresh PRBC supernatant (148±20 mg/dl and 0.50±0.05%, respectively; P<0.001, values differ versus fresh PRBC for both parameters), but the levels remained below values required by the Food and Drug Administration for stored human blood.

Potassium and lactate concentrations were greater in supernatant of stored PRBCs than in fresh PRBCs, whereas the pH was less. The $PO_2$ was greater in stored than in fresh PRBCs. As described previously (Bunn, Science 1971; 172:1049-5), levels of 2,3-DPG measured in ovine erythrocytes were very low. Intra-erythrocytic levels of 2,3-DPG did not differ between fresh and stored PRBCs. The $P_{50}$ did not differ between fresh and stored PRBCs. After leukoreduction, leukocytes were not detectable in PRBCs. Thus, ovine PRBCs showed many similar storage properties in AS-1 when compared to previous studies of human PRBC storage.

In Vivo Survival of Leukoreduced and AS-1-Stored Lamb PRBC

Figure 7:
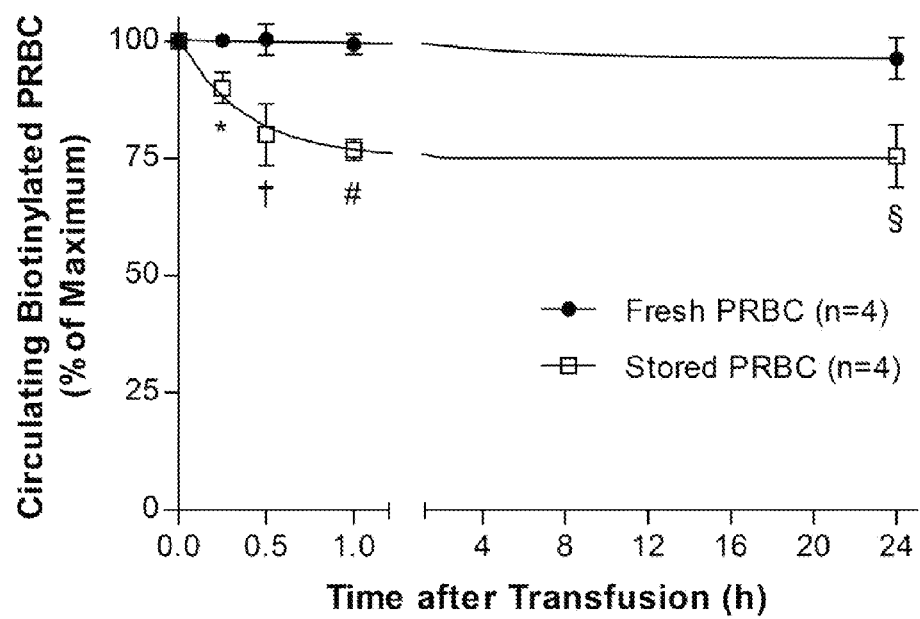
FIG. 7 is a graph depicting in vivo survival of leukoreduced ovine PRBC stored in additive solution-1. Circulating biotinylated PRBC are depicted on the y-axis. 96±4% of biotinylated fresh PRBC survived the first 24 h after transfusion, whereas 76±7% of biotinylated stored PRBC were circulating 24 h after transfusion. *P=0.001, value differs from fresh PRBC, †P=0.002, value differs from fresh PRBC, #P<0.001, value differs from fresh PRBC, §P=0.002, value fresh PRBC differs from stored PRBC. PRBC=packed erythrocytes. All data mean±SD.

PRBCs were biotinylated and transfused after 2 or 40 days of storage. Survival curves for circulating biotinylated PRBC are shown in FIG. 7. When fresh PRBCs were biotinylated and transfused, 96±4% survived for at least 24 h, whereas 76±7% of stored PRBCs remained in the circulation at 24 h after transfusion (P=0.002, values differ). Nearly all of the loss of biotinylated stored PRBCs occurred during the first hour after transfusion, with only 77±2% remaining 1 h after transfusion. Between 1 h and 24 h after transfusion, the circulating levels of labeled fresh and stored PRBC remained stable (stored PRBC: 77±2% after 1 h and 76±7% after 24 h, P=0.72; fresh PRBC: 99±2% after 1 h and 96±4% after 24 h, P=0.26). One week after transfusion, 80±8% and 54±4% of biotinylated fresh and stored PRBCs, respectively, remained in circulation. Thus, in vivo survival properties of ovine PRBCs after storage and transfusion are similar to those measured in human PRBCs.

Hemodynamic Effects of Transfusing Stored PRBC in Awake Lambs

Figure 8:
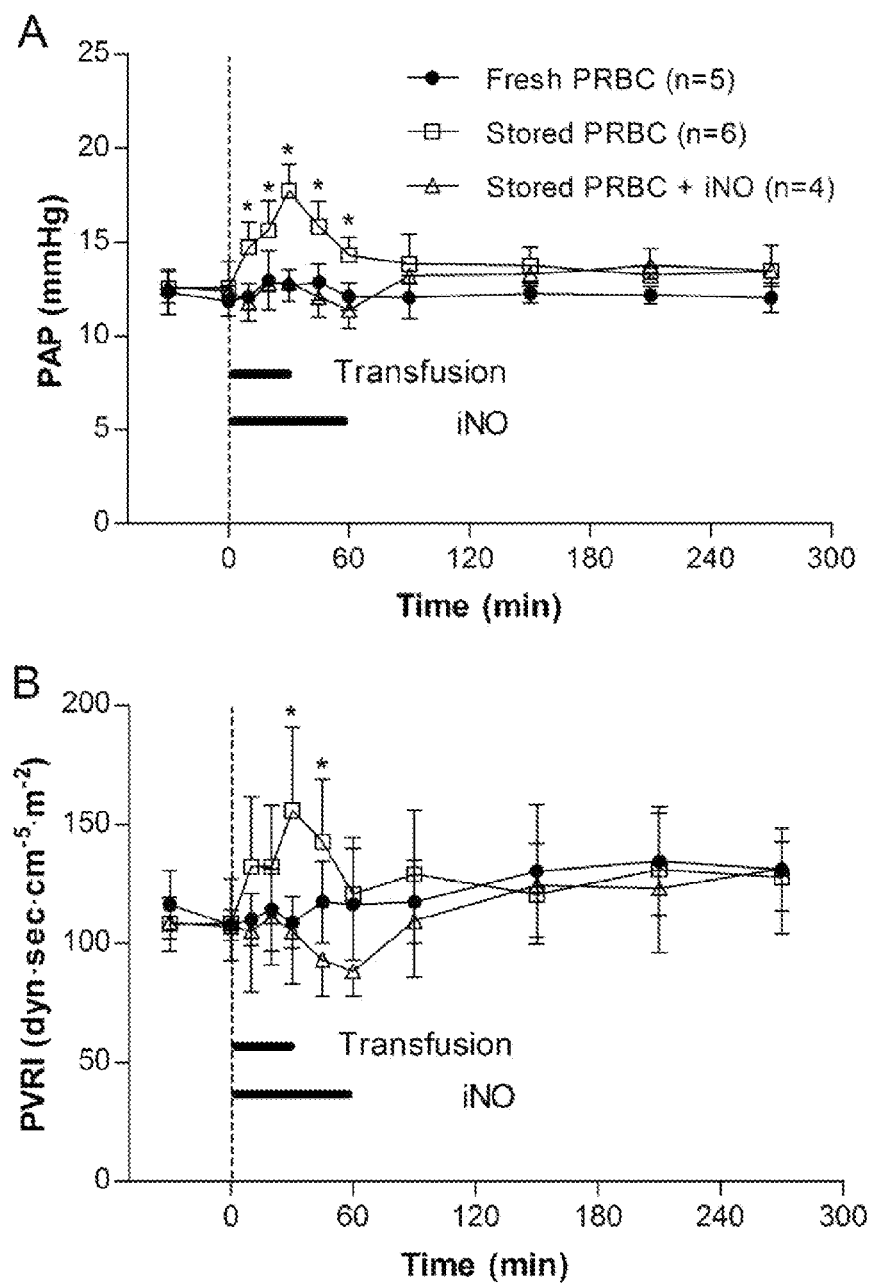
FIGS. 8A-8B are graphs depicting (A) Mean pulmonary arterial pressure and (B) pulmonary vascular resistance index measured during and after transfusion of fresh and stored PRBC in awake lambs. Some lambs received inhaled nitric oxide during and after transfusion of stored PRBC. *P<0.05, stored PRBC value differs from both fresh PRBC and stored PRBC+iNO, ANOVA. iNO=inhaled nitric oxide; PAP=mean pulmonary arterial pressure; PRBC=packed erythrocytes; PVRI=pulmonary vascular resistance index. All data mean±SD.

The effects of stored PRBC transfusion on PAP and PVRI differed from the effects of fresh PRBC transfusion (one-way ANOVA, P<0.001 for PAP and P=0.02 for PVRI, FIG. 8). Transfusion of fresh PRBC did not alter any of the measured hemodynamic parameters from baseline. Transfusion of stored PRBC increased PAP (baseline 13±1 versus 18±1 mmHg, P<0.001) and PVRI (baseline 108±19 versus 156±35 dyn·sec·cm$^{-5}$·m$^{-2}$, P=0.02), with both parameters peaking at the end of transfusion (FIG. 8). Both PAP and PVRI returned to baseline values 60 min after transfusion ended (FIG. 8). All other hemodynamic parameters measured did not change after transfusion of stored PRBCs. Therefore, transfusion of stored PRBCs increased pulmonary, but not systemic vascular pressures and resistances in lambs.

Figure 9:
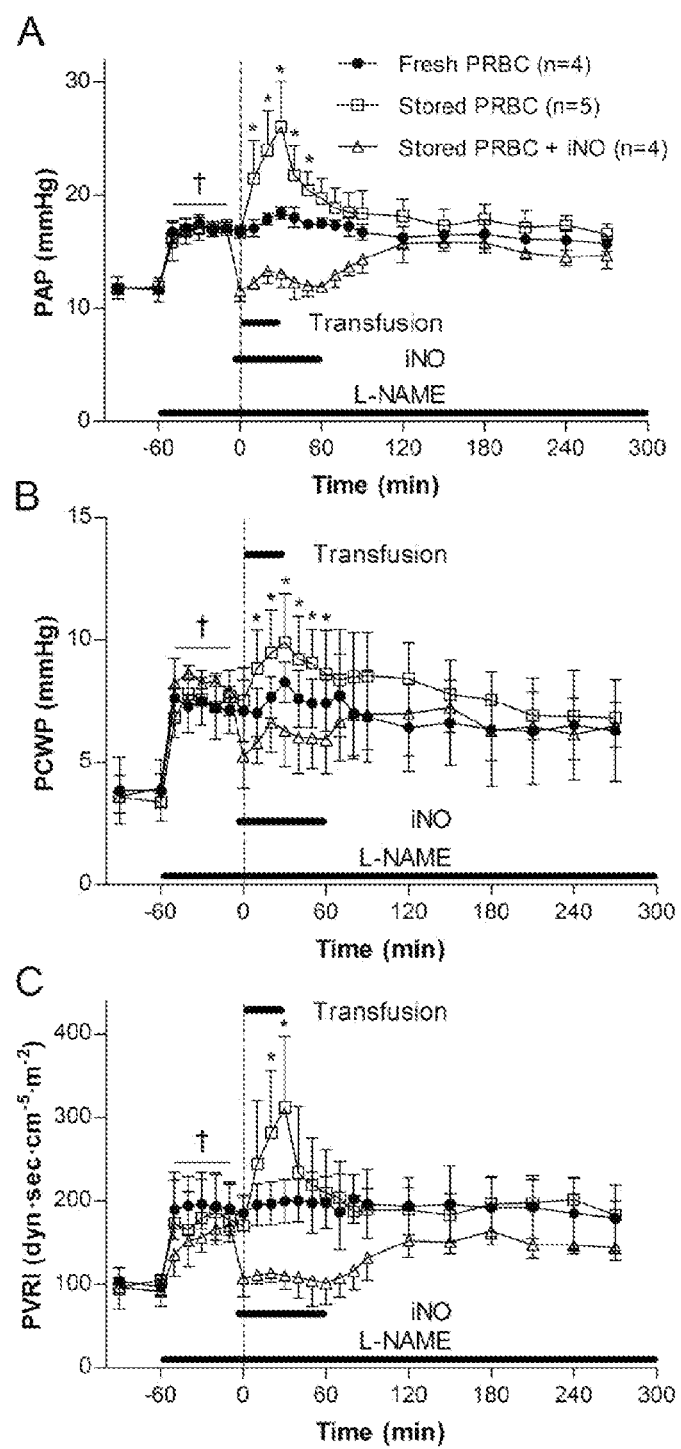
FIGS. 9A-9C are graphs depicting (A) Mean pulmonary arterial pressure, (B) pulmonary capillary wedge pressure, and (C) pulmonary vascular resistance index measured during and after transfusion of fresh and stored PRBC. Some lambs received inhaled nitric oxide during and after transfusion of stored PRBC. *P<0.05, stored PRBC value differs from both fresh PRBC and stored PRBC+iNO, ANOVA. L-NAME was administered prior to transfusion in order to induce endothelial dysfunction (†P<0.05, measurements at −60 min (before L-NAME) differ from measurements between −50 and −10 min in each group). iNO=inhaled nitric oxide; L-NAME=NG-nitro-L-arginine methyl-ester; PAP=mean pulmonary arterial pressure; PCWP=pulmonary capillary wedge pressure; PRBC=packed erythrocytes; PVRI=pulmonary vascular resistance index. All data mean±SD.

Hemodynamic Effects of Stored PRBC Transfusion in a Lamb Model of L-NAME-Induced Endothelial Dysfunction To investigate whether endothelial dysfunction alters the pulmonary vasoconstrictor response to transfusion of stored PRBC, lambs were pretreated with L-NAME. A dose of L-NAME was infused that partially inhibited NOS activity, as reflected by a 50% reduction in the ability of acetylcholine infusion to induce systemic vasodilation. As anticipated, L-NAME administration did not alter the vasodilator response to an intravenous bolus infusion of sodium nitroprusside. Infusion of L-NAME increased MAP, PAP, central venous pressure, and PCWP, as well as systemic and pulmonary vascular resistance indices, whereas both cardiac index and heart rate decreased (FIG. 9).

Transfusion of fresh PRBCs did not alter any measured hemodynamic parameter. In contrast, transfusion of stored PRBCs increased PAP (baseline 17±1 versus 26±4 mmHg, P<0.001), PCWP (baseline 7±1 versus 10±2 mmHg, P=0.02), and PVRI (baseline 170±34 versus 312±85 dyn·sec·cm$^{-5}$·m$^{-2}$, P=0.009) in L-NAME-treated awake lambs (FIG. 9). The increase in PAP and PVRI induced by transfusing stored PRBCs was greater in the presence of L-NAME than without L-NAME (Δ PAP without L-NAME 5±1 mmHg differs from Δ PAP with L-NAME 9±4 mmHg, P=0.03; Δ PVRI without L-NAME 47±33 dyn·sec·cm$^{-5}$·m$^{-2}$ differs from Δ PVRI with L-NAME 142±53 dyn·sec·cm$^{-5}$·m$^{-2}$, P=0.006). MAP was not statistically different between groups (one-way ANOVA, P=0.09). Hence, partial inhibition of NOS potentiated the vasoconstrictor effect of stored PRBCs on the pulmonary, but not the systemic circulation.

Concurrent Inhalation of Nitric Oxide During Transfusion of Stored PRBCs

Inhaled nitric oxide prevents pulmonary vasoconstriction during infusion of HBOC-201 (Yu et al., Anesthesiology 2009; 110:113-2). To examine whether breathing nitric oxide prevents the pulmonary vasoconstrictor response to transfusion of stored PRBCs, 80 ppm nitric oxide was administered concurrently during transfusion and for 30 min thereafter. In lambs, which were not pretreated with L-NAME, breathing nitric oxide prevented the increase of PAP (baseline 12±1 versus 13±1 mmHg, P=0.13) and PVRI (baseline 107±14 versus 105±22 dyn·sec·cm$^{-5}$·m$^{-2}$, P=0.87) associated with transfusion of stored PRBCs (FIG. 8).

In lambs pretreated with L-NAME, concurrent inhalation of 80 ppm nitric oxide reduced the PAP and PVRI to baseline, and prevented the pulmonary vasoconstriction observed with transfusion of stored PRBCs. After nitric oxide breathing ceased at 30 min after transfusion, PAP and PVRI gradually increased, returning to pre-transfusion levels 60 min after nitric oxide breathing ended (FIGS. 9A and 9C). As expected, inhalation of nitric oxide did not alter MAP (one-way ANOVA, P=0.89). Thus, nitric oxide breathing prevented the pulmonary vasoconstrictor effects associated with transfusion of stored PRBCs in lambs.

Figure 10:
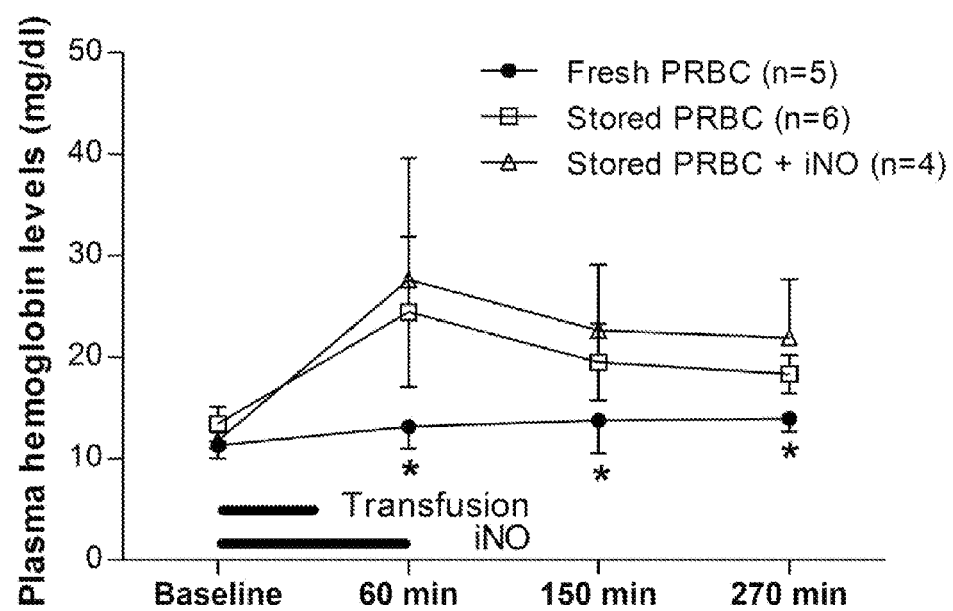
FIG. 10 is a graph depicting plasma hemoglobin levels measured before and after transfusion of fresh and stored PRBC in healthy awake lambs. Some lambs received inhaled nitric oxide during and after transfusion of stored PRBC. *P<0.05, fresh PRBC value differs from both stored PRBC and stored PRBC+iNO, ANOVA. iNO=inhaled nitric oxide; PRBC=packed erythrocytes. All data mean±SD.

Potential Mechanisms for the Pulmonary Hypertension Caused by Transfusing Stored PRBCs To elucidate the mechanisms potentially responsible for the pulmonary vasoconstriction observed after transfusion of stored PRBC, cell-free hemoglobin concentrations in ovine plasma were measured before and after transfusion of fresh and stored PRBC. Transfusion with fresh PRBCs did not alter cell-free hemoglobin levels (FIG. 10). In contrast, transfusion of stored PRBCs increased cell-free hemoglobin levels at 60 min with levels remaining elevated for up to 4.5 h. Breathing nitric oxide did not alter the ability of transfusing stored PRBCs to increase cell-free hemoglobin.

Compared to humans, sheep have a low plasma concentration of the hemoglobin-scavenger Hp (Kallapur et al., Am J Respir Crit Care Med 2009; 179:955-61). Plasma levels of Hp decreased after transfusion of either fresh or stored PRBCs. However, a more pronounced decrease of Hp was measured after transfusion of stored PRBCs (two-way ANOVA comparing fresh PRBC with stored PRBC over time, P=0.002).

Thromboxane $B_2$ ($TXB_2$) is the stable metabolite of the potent vasoconstrictor thromboxane $A_2$. Release of thromboxane metabolites by pulmonary intravascular macrophages can induce pronounced pulmonary hypertension (Staub, Annu Rev Physiol 1994; 56:47-67). To determine whether the increase of PAP and pulmonary vascular resistance induced by transfusing stored PRBCs was mediated by increased plasma concentrations of thromboxane metabolites, $TXB_2$ levels were measured before and after transfusion of fresh and stored PRBCs. Plasma concentrations of $TXB_2$ did not differ before and at 30 min after transfusion of either fresh or stored PRBCs, providing evidence that thromboxane is unlikely to be responsible for the pulmonary hypertension associated with transfusion of stored PRBCs.

Figure 11:
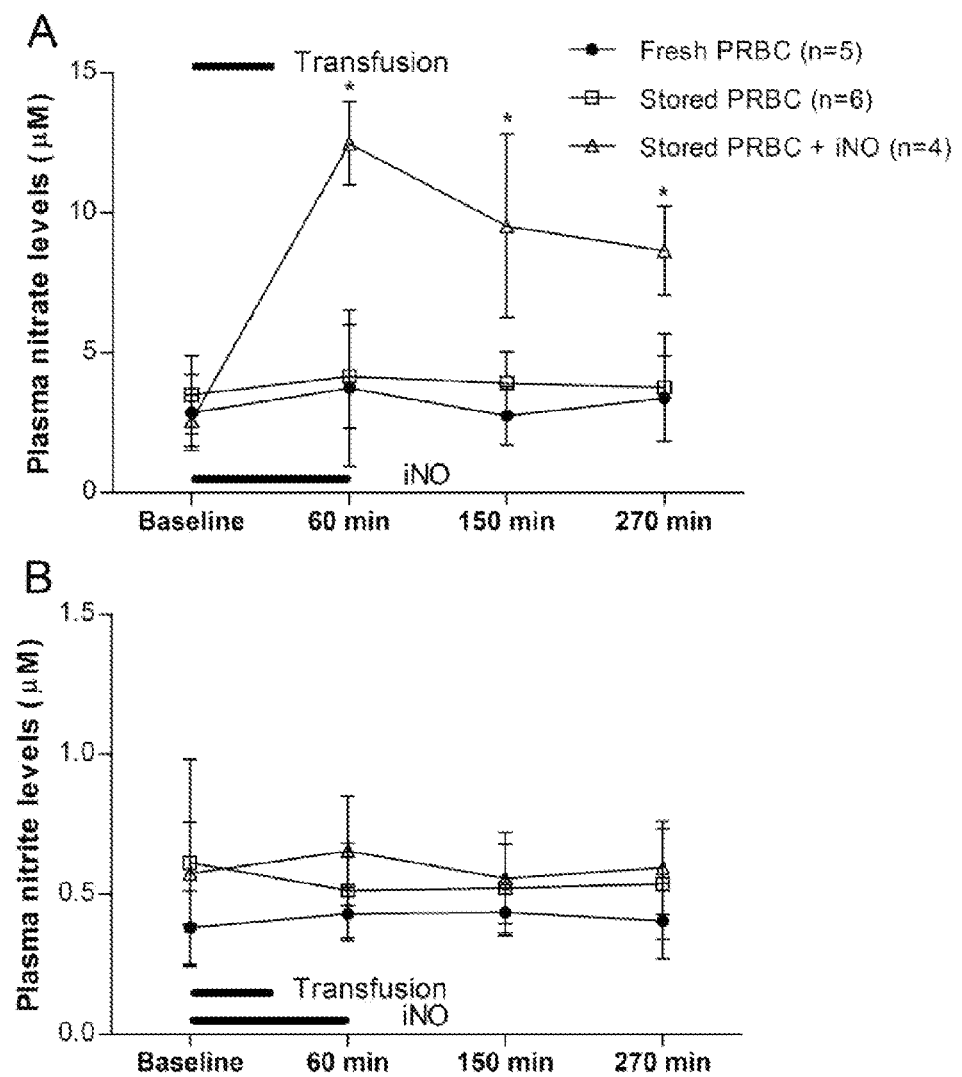
FIGS. 11A-11B are graphs depicting plasma (A) nitrate and (B) nitrite levels measured before and after transfusion of fresh and stored PRBC in awake lambs. *P<0.05, stored PRBC+iNO value differs from both fresh PRBC and stored PRBC, ANOVA. iNO=inhaled nitric oxide; PRBC=packed erythrocytes. All data mean±SD.

Nitrite can be converted to nitric oxide via nitrite reductases (Weitzberg et al., Anesthesiology 2010; 113:1460-75). Depletion of plasma nitrite after transfusion might therefore be associated with transfusion of stored PRBCs. To examine if transfusion of PRBCs resulted in changes of plasma nitric oxide metabolites, levels of plasma nitrate and nitrite were measured after transfusion of fresh and stored PRBCs. Plasma nitrate and nitrite levels did not differ before or after transfusion of fresh or stored PRBC (two-way ANOVA, P=0.37 for nitrate and P=0.21 for nitrite; FIG. 11).

Transfusion of Leukoreduced and AS-1-Stored Lamb PRBC does not Induce Systemic Inflammation In order to determine whether transfusion of autologous PRBCs results in an inflammatory response, plasma IL-6 concentrations were measured as well as lung and liver levels of mRNAs encoding IL-6, tumor necrosis factor-α, and myeloperoxidase before and after transfusion of either fresh or stored PRBCs. Neither plasma IL-6 levels nor levels of mRNAs encoding inflammatory mediators were altered by transfusing fresh or stored PRBCs. Leukocyte concentrations measured before and after transfusion of fresh or stored PRBCs did not differ. Thus, transfusion of autologous and leukoreduced fresh or stored PRBCs did not induce an inflammatory response in this lamb model within 4 h after transfusion.

Example 3

Figure 12:
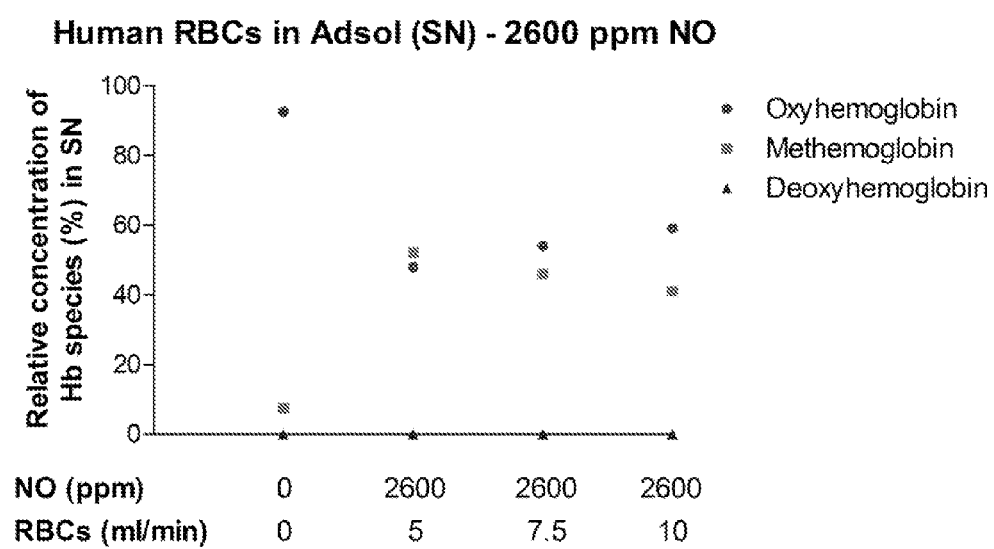
FIG. 12 is a graph depicting the relative concentration of hemoglobin species in red blood cell supernatant treated with gaseous nitric oxide in nitrogen via a microporous gas exchanger.
Figure 13:
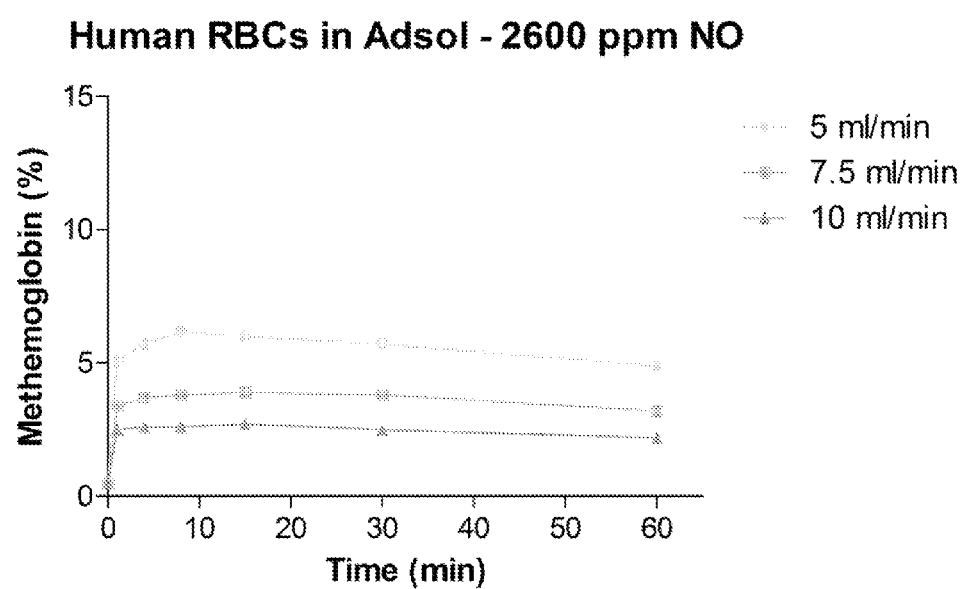
FIG. 13 is a graph depicting the relative concentration of methemoglobin in red blood cells treated with gaseous nitric oxide in nitrogen via a microporous gas exchanger.

Methemoglobin Conversion Following Treatment of Red Blood Cells with Nitric Oxide Plasma containing added human hemoglobin was added to adsol-preserved human red blood cells. The red blood cells were pumped (at flow rates of 5, 7.5, and 10 ml/min) through a membrane gas exchanger (Living Systems instrumentation Inc., St. Albans, Vt.), which exposed the cells (on a single pass through the gas exchanger) to 2600 ppm nitric oxide gas in nitrogen. The nitric oxide treatment resulted in approximately 50% of supernatant oxyhemoglobin being converted to methemoglobin (FIG. 12). However, since human red cells contain large quantities of the enzyme methemoglobin reductase, the nitric oxide treatment caused only a few percent of human red cell hemoglobin to be converted to methemoglobin (FIG. 13).

Example 4

Treatment of Stored Red Blood Cells with a Nitric Oxide-Releasing Compound

Figure 14A:
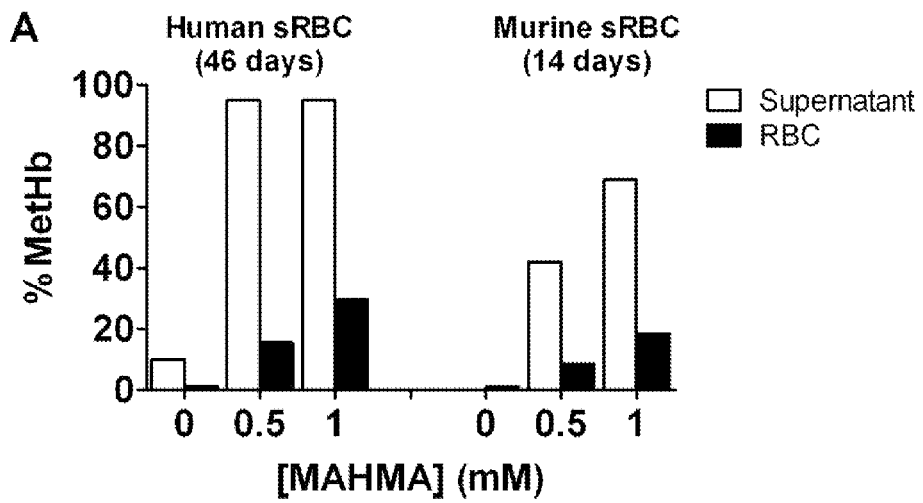
FIGS. 14A-14B are graphs depicting the effects of MAHMA/NO treatment on human and murine stored red blood cells. A) Oxidation of supernatant cell-free hemoglobin compared with intracellular red blood cell levels of methemoglobin. B) Concentration of hemoglobin in the supernatant ([Hb], μM) and in the red blood cells (Hct, %).
Figure 14B:
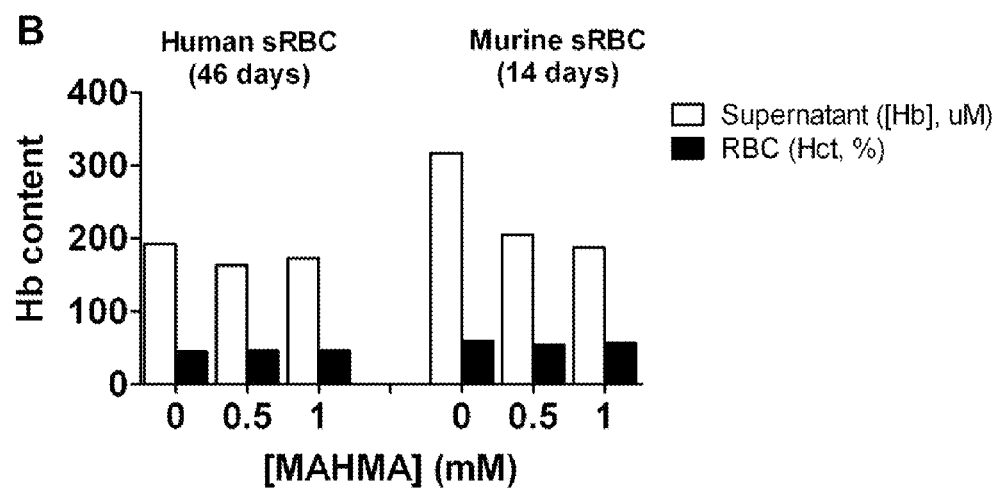

Human stored red blood cells (stored, 46 days) were treated with MAHMA/NO ((Z)-1-[N-Methyl-N-[6-(N-methylammoniohexyl)amino]]diazen-1-ium-1,2-diolate). Treatment with 0.5 mM MAHMA/NO resulted in 99% of the supernatant hemoglobin being oxidized to methemoglobin (FIG. 14A). In contrast, only 15% of the red blood cell hemoglobin was oxidized by this treatment (FIG. 14A). In addition, no further hemolysis of the human stored red blood cells occurred after addition of MAHMA/NO (FIG. 14B).

Studies with murine stored red blood cells (stored, 14 days) indicated that a greater amount of MAHMA/NO was required to increase the amount of oxidized supernatant (1 mM MAHMA/NO resulted in 70% supernatant methemoglobin; FIG. 14A). This is likely due to the higher levels of hemolysis observed in murine red blood cell storage. At baseline levels, hemolysis is higher than in human stored red blood cells, and increasing concentrations of MAHMA/NO were required to fully oxidize the cell-live hemoglobin. The level of cell-tree hemoglobin in the supernatant of murine stored red blood cells varies, and decreases upon addition of MAHMA/NO (FIG. 14B).

Figure 15:
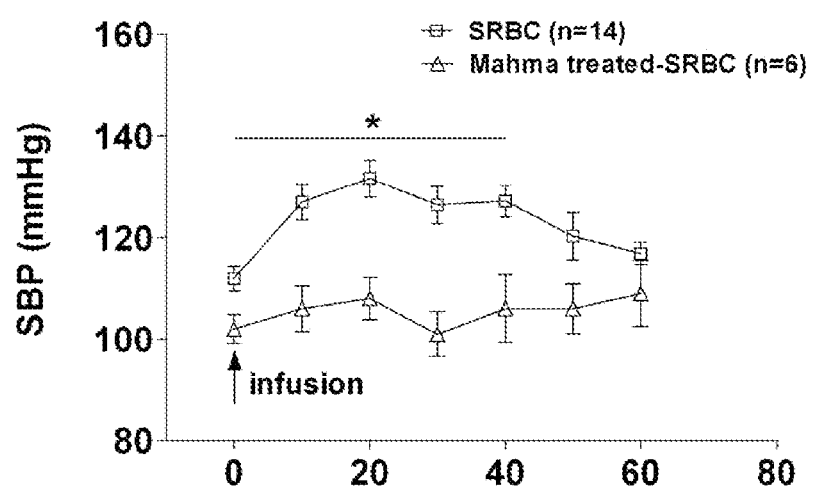
FIG. 15 is a graph depicting systolic blood pressure (mmHg) measured by non-invasive tail-cuff before and after infusion into awake db/db mice either stored red blood cells (stored for 2 weeks) or stored red blood cells pre-treated with 1 mM MAHMA/NO, 5% v/v. *P<0.05 differs versus SRBC pre-treated with MAHMA/NO.

Murine stored red blood cells were pretreated with 1 mM MAHMA before infusion into db/db mice. A total of 8 db/db mice were studied, in two groups: stored red blood cells (n=2; SRBC), pre-treated stored red blood cells (n=6; Mahma treated-SRBC). Pre-treatment of the stored red blood cells with MAHMA/NO attenuated the hypertensive effect caused by infusion of stored red blood cells into db/db mice (FIG. 15).

Example 5

Membranes for Use in Ex Vivo Nitric Oxide Treatment of Red Blood Cells

Figure 16:
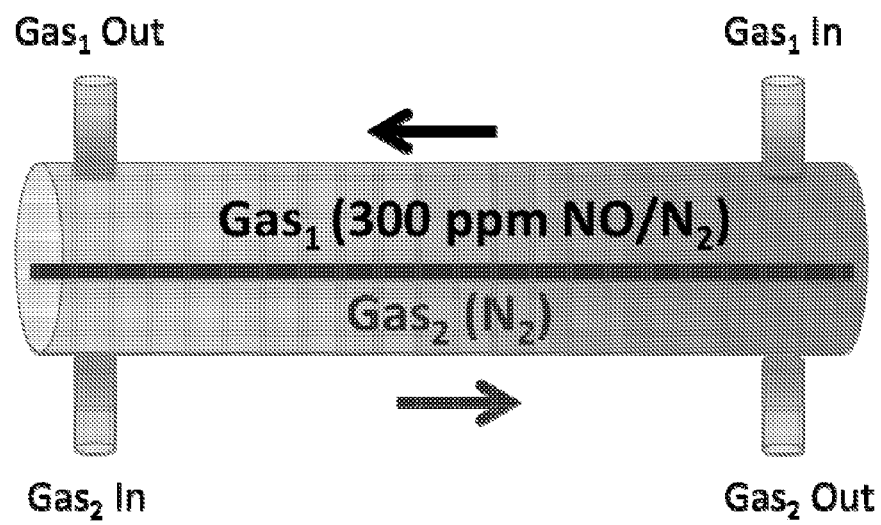
FIG. 16 depicts a membrane-containing device used for gas to gas transfer experiments.
Figure 17:
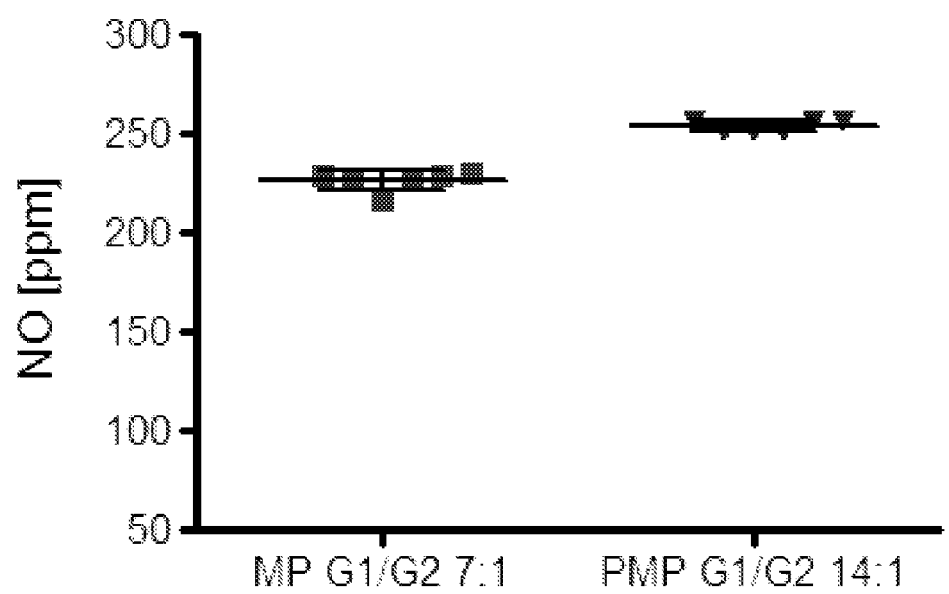
FIG. 17 is a graph depicting nitric oxide concentrations measured across microporous (MP) and polymethylpentene (PMP) membranes at various gas flow ratios (data are presented as mean±SD, n=6; G1/G2 7:1; gas flow ratios at 7:1; G1/G2 14:1; gas flow ratios at 14:1).

The rate of transport of gaseous nitric oxide across commercially available membranes was assessed in a gas to gas study, using a microporous (MP) membrane (Micro-1 Rat Oxygenator, Kewei Rising, Shenzhen, Guangdong Province, China) and a polymethylpentene (PMP) membrane oxygenator (Quadrox-iD Pediatric Oxygenators, MAQUET Cardiovascular, Wayne, N.J.). Assessment of the membranes was performed using countercurrent streams of (i) 300 parts per million (ppm) nitric oxide in nitrogen (to avoid oxidation to $NO_2$) in the gas phase and (ii) pure nitrogen gas in the other phase, which was usually blood (FIG. 16). The MP membrane allowed almost total equilibration of nitric oxide levels across the device (FIG. 17). The PMP membrane also performed well, with nitric oxide levels approaching the gas phase nitric oxide level of 300 ppm (FIG. 17). Thus, PMP and MP membranes may be used to expose blood to nitric oxide as a means to oxidize extracellular methemoglobin.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a red blood cell sample, the method comprising contacting a red blood cell sample ex vivo with an amount of nitric oxide or a nitric oxide-releasing compound sufficient to convert at least 20% of extracellular ferrous hemoglobin present in the red blood cell sample to ferric hemoglobin, wherein less than 20% of hemoglobin present in red blood cells in the red blood cell sample is converted to methemoglobin.

2. The method of claim 1, wherein the red blood cell sample has been subjected to hemodialysis, intraoperative blood salvage, or cardiotomy suction ex vivo prior to being contacted with nitric oxide or the nitric oxide-releasing compound.

3. The method of claim 1, wherein the red blood cell sample has been subjected to one or more of a pump, a membrane, or air bubbles ex vivo prior to being contacted with nitric oxide or the nitric oxide-releasing compound.

4. The method of claim 1, wherein the red blood cell sample has been stored ex vivo for at least 24 hours after removal from a donor and prior to being contacted with nitric oxide or the nitric oxide-releasing compound.

5. The method of claim 1, wherein the red blood cell sample has been stored ex vivo for at least 7 days after removal from a donor and prior to being contacted with nitric oxide or the nitric oxide-releasing compound.

6. The method of claim 1, wherein the red blood cell sample has been stored ex vivo for at least 14 days after removal from a donor and prior to being contacted with nitric oxide or the nitric oxide-releasing compound.

7. The method of claim 1, wherein the red blood cell sample has been stored ex vivo for at least 28 days after removal from a donor and prior to being contacted with nitric oxide or the nitric oxide-releasing compound.

8. The method of claim 1, wherein the red blood cell sample has been stored ex vivo for at least 42 days after removal from a donor and prior to being contacted with nitric oxide or the nitric oxide-releasing compound.

9. The method of claim 1, wherein the red blood cell sample is contacted with a therapeutic gas comprising gaseous nitric oxide.

10. The method of claim 9, wherein the concentration of gaseous nitric oxide in the therapeutic gas is at least 20 ppm.

11. The method of claim 9, wherein the red blood cell sample is contacted with the therapeutic gas for fewer than 5 seconds.

12. The method of claim 1, wherein the red blood cell sample is contacted with a nitric oxide-releasing compound.

13. The method of claim 1, wherein the method is performed under sterile conditions.

14. The method of claim 1, wherein at least 50% of extracellular ferrous hemoglobin present in the red blood cell sample is converted to ferric hemoglobin.

15. The method of claim 1, wherein at least 80% of extracellular ferrous hemoglobin present in the red blood cell sample is converted to ferric hemoglobin.

16. The method of claim 1, wherein less than 15% of hemoglobin present in red blood cells in the red blood cell sample is converted to methemoglobin.

17. The method of claim 1, wherein less than 10% of hemoglobin present in red blood cells in the red blood cell sample is converted to methemoglobin.

18. The method of claim 1, wherein less than 5% of hemoglobin present in red blood cells in the red blood cell sample is converted to methemoglobin.

19. The method of claim 9, wherein the concentration of gaseous nitric oxide in the therapeutic gas is at least 40 ppm.

20. The method of claim 9, wherein the concentration of gaseous nitric oxide in the therapeutic gas is at least 80 ppm.

21. The method of claim 9, wherein the concentration of gaseous nitric oxide in the therapeutic gas is in the range of 100 ppm to 800 ppm.

22. The method of claim 9, wherein the concentration of gaseous nitric oxide in the therapeutic gas is in the range of 40 ppm to 200 ppm.

23. The method of claim 9, wherein the concentration of gaseous nitric oxide in the therapeutic gas is in the range of 40 ppm to 3,000 ppm.

24. The method of claim 9, wherein the red blood cell sample is contacted with the therapeutic gas for at least 15 minutes.

25. The method of claim 9, wherein the red blood cell sample is contacted with the therapeutic gas for at least one hour.

26. The method of claim 9, wherein the red blood cell sample is contacted with the therapeutic gas for at least two hours.

27. The method of claim 12, wherein the nitric oxide-releasing compound comprises nitrite.

28. The method of claim 12, wherein the nitric oxide-releasing compound is an ultra-short-acting nitric oxide-releasing compound.

29. The method of claim 28, wherein the ultra-short-acting nitric oxide-releasing compound is 1-[2-(carboxylato)pyrrolidin-1-yl]diazen-1-ium-1,2-diolate or (Z)-1-[N-Methyl-N-[6-(N-methylammoniohexyl)amino]]diazen-1-ium-1,2-diolate.

* * * * *